(12) United States Patent
Srinivasan et al.

(10) Patent No.: US 12,415,909 B2
(45) Date of Patent: Sep. 16, 2025

(54) OIL-CONTAINING RUBBER COMPOSITIONS AND RELATED METHODS

(71) Applicant: Bridgestone Americas Tire Operations, LLC, Nashville, TN (US)

(72) Inventors: Priyavardhana Srinivasan, Akron, OH (US); Amy M. Randall, Brentwood, TN (US); Justin J. Styer, Cortland, OH (US); Lawrence T. Rittman, Canton, OH (US)

(73) Assignee: Bridgestone Americas Tire Operations, LLC, Nashville, TN (US)

( * ) Notice: Subject to any disclaimer, the term of this patent is extended or adjusted under 35 U.S.C. 154(b) by 50 days.

(21) Appl. No.: 18/333,413

(22) Filed: Jun. 12, 2023

(65) Prior Publication Data
US 2023/0331965 A1 Oct. 19, 2023

Related U.S. Application Data

(63) Continuation of application No. 17/322,132, filed on May 17, 2021, now Pat. No. 11,674,020, which is a continuation of application No. 16/528,576, filed on Jul. 31, 2019, now Pat. No. 11,008,448, which is a continuation of application No. 15/539,050, filed as application No. PCT/US2015/064503 on Dec. 8, 2015, now Pat. No. 10,370,526.

(60) Provisional application No. 62/095,955, filed on Dec. 23, 2014.

(51) Int. Cl.
| | |
|---|---|
| C08L 9/06 | (2006.01) |
| B60C 1/00 | (2006.01) |
| C08K 3/00 | (2018.01) |
| C08L 9/00 | (2006.01) |
| C08L 15/00 | (2006.01) |
| C12P 7/64 | (2022.01) |
| C12P 7/6463 | (2022.01) |

(52) U.S. Cl.
CPC .................. C08L 9/06 (2013.01); B60C 1/00 (2013.01); B60C 1/0016 (2013.01); C08K 3/00 (2013.01); C08L 9/00 (2013.01); C08L 15/00 (2013.01); C12P 7/64 (2013.01); C12P 7/6463 (2013.01)

(58) Field of Classification Search
None
See application file for complete search history.

(56) References Cited

U.S. PATENT DOCUMENTS

| | | | |
|---|---|---|---|
| 5,252,649 A | 10/1993 | Hausmann | |
| 5,504,164 A | 4/1996 | O'Donnell | |
| 5,512,638 A | 4/1996 | O'Donnell | |
| 5,624,990 A | 4/1997 | Vipperman | |
| 5,650,454 A | 7/1997 | Hoover et al. | |
| 5,717,022 A | 2/1998 | Beckmann et al. | |
| 5,877,244 A | 3/1999 | Hoover et al. | |
| 6,231,026 B1 | 5/2001 | Patitsas et al. | |
| 6,380,291 B1 | 4/2002 | Von Hellens | |
| 6,448,313 B1 | 9/2002 | Patel | |
| 6,759,456 B2 | 7/2004 | Kikuchi | |
| 6,822,043 B2 | 11/2004 | Sohnen et al. | |
| 6,831,119 B2 | 12/2004 | Brown et al. | |
| 6,998,088 B2 | 2/2006 | Beers et al. | |
| 7,041,719 B2 | 5/2006 | Kriesel et al. | |
| 7,119,147 B2 | 10/2006 | Kikuchi | |
| 7,193,004 B2 | 3/2007 | Weydert et al. | |
| 7,211,611 B2 | 5/2007 | Wilson, III | |
| 7,247,663 B2 | 7/2007 | Kikuchi et al. | |
| 7,253,225 B2 | 8/2007 | Labauze et al. | |
| 7,275,572 B2 | 10/2007 | Kikuchi et al. | |
| 7,285,584 B2 | 10/2007 | Hsu et al. | |
| 7,335,692 B2 | 2/2008 | Vasseur et al. | |
| 7,411,018 B2 | 8/2008 | Appel et al. | |
| 7,432,318 B2 | 10/2008 | Kikuchi | |
| 7,473,724 B2 | 1/2009 | Hsu et al. | |
| 7,484,544 B2 | 2/2009 | Serra et al. | |
| 7,709,560 B2 | 5/2010 | Yagi et al. | |
| 7,714,041 B2 | 5/2010 | Schmitz et al. | |
| 7,714,051 B2 | 5/2010 | Hahn | |
| 7,825,183 B2 | 11/2010 | Robert et al. | |
| 7,855,243 B2 | 12/2010 | Kanz et al. | |
| 7,882,874 B2 | 2/2011 | Robert et al. | |
| 7,906,602 B2 | 3/2011 | Schmitz et al. | |
| 7,946,323 B2 | 5/2011 | Kikuchi et al. | |
| 8,044,118 B2 | 10/2011 | Sakaki et al. | |
| 8,044,131 B2 | 10/2011 | Hirayama et al. | |

(Continued)

FOREIGN PATENT DOCUMENTS

| | | |
|---|---|---|
| CN | 102174218 B | 1/2013 |
| DE | 19700967 C2 | 4/2000 |

(Continued)

OTHER PUBLICATIONS

International Search Report from PCT application PCT/US2015/064503 dated Jan. 2015 (4 pages).
International Preliminary Report on Patentability with Written Opinion from PCT application PCT/US2015/064503 dated Jun. 2017 (10 pages).
Robertson, et al., "Effect of Planting Date on Sunflower Seed Content, Fatty Acid Composition and Yield in Florida," Journal of the American Oil Chemists' Society, Jun. 1981, vol. 58, Issue 6, pp. 698-701.
Unger, Paul, W., "Planting Date Effects On Growth, Yield, And Oil of Irrigated Sunflower," Agronomy Journal, vol. 72, Nov.-Dec. 1980, pp. 914-916.

(Continued)

*Primary Examiner* — Vu A Nguyen
(74) *Attorney, Agent, or Firm* — Meredith E. Hooker; Jenny L. Sheaffer

(57) ABSTRACT

Disclosed herein are rubber compositions comprising bio-oil produced by a recombinant cell. Also disclosed are methods of controlling the variability of fatty acid content in bio-oil containing rubber compositions or tires comprising at least one component incorporating the bio-oil containing rubber composition, and a method of providing a bio-oil-containing tire with a reduced carbon footprint.

25 Claims, No Drawings

(56) References Cited

U.S. PATENT DOCUMENTS

| | | | |
|---|---|---|---|
| 8,100,157 B2 | 1/2012 | Hattori et al. | |
| 8,101,679 B2 | 1/2012 | Knobloch et al. | |
| 8,236,875 B2 | 8/2012 | Recker et al. | |
| 8,324,310 B2 | 12/2012 | Robert et al. | |
| 8,426,508 B2 | 4/2013 | Hattori et al. | |
| 8,426,512 B2* | 4/2013 | Zhang | C08L 19/006 152/209.5 |
| 8,476,342 B2 | 7/2013 | Colvin et al. | |
| 8,487,014 B1 | 7/2013 | Flanigan et al. | |
| 8,563,628 B2 | 10/2013 | Sakaki et al. | |
| 8,614,276 B2 | 12/2013 | Voge et al. | |
| 8,669,321 B2 | 3/2014 | Hattori et al. | |
| 8,697,762 B2 | 4/2014 | Flanigan et al. | |
| 8,710,140 B2 | 4/2014 | Pialot et al. | |
| 8,957,132 B2 | 2/2015 | Voge et al. | |
| 8,969,454 B2 | 3/2015 | Bastioli et al. | |
| 9,169,362 B2 | 10/2015 | Brown et al. | |
| 9,243,133 B2 | 1/2016 | Voge et al. | |
| 9,393,837 B2 | 7/2016 | Voge et al. | |
| 9,683,089 B2 | 6/2017 | Brown et al. | |
| 2005/0145312 A1 | 7/2005 | Herberger, Sr. et al. | |
| 2006/0125146 A1 | 6/2006 | Sandstrom | |
| 2006/0231183 A1 | 10/2006 | Serra et al. | |
| 2009/0005481 A1 | 1/2009 | Ishida et al. | |
| 2009/0048400 A1 | 2/2009 | Jung et al. | |
| 2009/0229720 A1 | 9/2009 | Serra et al. | |
| 2011/0112213 A1 | 5/2011 | Recker et al. | |
| 2011/0233479 A1 | 9/2011 | Korzhenko et al. | |
| 2013/0096248 A1 | 4/2013 | Thompson et al. | |
| 2013/0153100 A1 | 6/2013 | Pifford et al. | |
| 2013/0172474 A1 | 7/2013 | Voge et al. | |
| 2013/0196085 A1 | 8/2013 | Voge et al. | |
| 2013/0274404 A1 | 10/2013 | Vasseur et al. | |
| 2013/0281611 A1 | 10/2013 | Recker et al. | |
| 2013/0289183 A1* | 10/2013 | Kerns | C08F 236/10 524/313 |
| 2013/0296471 A1 | 11/2013 | Lesage et al. | |
| 2013/0299053 A1 | 11/2013 | Fugier et al. | |
| 2014/0024745 A1 | 1/2014 | Sandstrom et al. | |
| 2014/0135424 A1 | 5/2014 | Sandstrom et al. | |
| 2014/0135437 A1 | 5/2014 | Sandstrom et al. | |
| 2014/0171557 A1 | 6/2014 | Ringot | |
| 2014/0235751 A1 | 8/2014 | Lesage et al. | |
| 2014/0243448 A1 | 8/2014 | Lesage et al. | |
| 2014/0355746 A1 | 12/2014 | Yasrebi et al. | |
| 2014/0357746 A1 | 12/2014 | Ngantung et al. | |
| 2014/0371346 A1 | 12/2014 | Saintigny et al. | |
| 2015/0087745 A1 | 3/2015 | Chekanov et al. | |
| 2015/0283854 A1 | 10/2015 | Saintigny et al. | |
| 2017/0058112 A1 | 3/2017 | Kerns et al. | |

FOREIGN PATENT DOCUMENTS

| | | |
|---|---|---|
| EP | 2028022 A1 | 2/2009 |
| EP | 2112003 B1 | 10/2009 |
| EP | 2030809 B1 | 11/2010 |
| EP | 2246200 A1 | 11/2010 |
| EP | 2340946 B1 | 11/2012 |
| EP | 2657262 A1 | 10/2013 |
| EP | 2733170 A1 | 5/2014 |
| EP | 2748248 A1 | 3/2018 |
| JP | 2007-099892 A | 4/2007 |
| JP | 2008-056802 A | 3/2008 |
| JP | 2009-114257 A | 5/2009 |
| KR | 10-0885080 B | 2/2009 |
| KR | 20090058061 A | 6/2009 |
| KR | 2012-0057074 A | 6/2012 |
| WO | 2009-11220 A1 | 9/2009 |
| WO | 2011/123406 A1 | 10/2011 |
| WO | 2013172699 A1 | 11/2013 |
| WO | 2014176515 A2 | 10/2014 |

OTHER PUBLICATIONS

European search opinion and extended European search report from EP application No. 15 874 098.5, dated Jul. 2, 2018 (7 pages).

* cited by examiner

OIL-CONTAINING RUBBER COMPOSITIONS AND RELATED METHODS

CROSS-REFERENCE TO RELATED APPLICATIONS

This application is a continuation of U.S. application Ser. No. 17/322,132 filed May 17, 2021 and assigned U.S. Pat. No. 11,674,020 and an issue date of Jun. 13, 2023, which is a continuation of U.S. application Ser. No. 16/528,576 filed Jul. 13, 2019 and assigned U.S. Pat. No. 11,008,448 and an issue date of May 18, 2021, which is a continuation of U.S. application Ser. No. 15/539,050, filed Jun. 22, 2017, and issued as U.S. Pat. No. 10,370,526 on Aug. 6, 2019, which is a U.S. national stage of International Application Number PCT/US2015/064503, filed on Dec. 8, 2015, which application claims priority to and any other benefit of U.S. Provisional Patent Application Ser. No. 62/095,955, filed Dec. 23, 2014, and entitled "OIL-CONTAINING RUBBER COMPOSITIONS AND RELATED METHODS," the entire disclosure of each of which is incorporated by reference herein.

FIELD OF THE DISCLOSURE

The present disclosure relates to rubber compositions comprising bio-oil produced by a recombinant cell. The disclosure also relates to methods of controlling the variability of fatty acid content in bio-oil containing rubber compositions or tires comprising at least one component incorporating the bio-oil containing rubber composition, and a method of providing a bio-oil-containing tire with a reduced carbon footprint.

BACKGROUND

Most rubber compositions that are intended for use in or used in a tire will incorporate some amount of oil, either processing oil, extender oil for one or more rubbers, or both. For many decades the oils utilized in such rubber compositions were primarily petroleum or fossil-fuel based. However, more recently bio-oils sourced from the components of various plants have been used in such rubber compositions.

SUMMARY

The present disclosure relates to rubber compositions comprising bio-oil produced by a recombinant cell. The disclosure also relates to methods of controlling the variability of fatty acid content in bio-oil containing rubber compositions or tires comprising at least one component incorporating the bio-oil containing rubber composition, and to a method of providing a bio-oil-containing tire with a reduced carbon footprint.

In a first embodiment, a method is disclosed for controlling the variability of fatty acid content in a bio-oil-containing rubber composition. The method comprises incorporating about 5 to about 100 phr of bio-oil produced by a recombinant cell with at least one rubber, at least one reinforcing filler, and a cure package, thereby forming a bio-oil-containing rubber composition.

In a second embodiment, a method is disclosed for providing a bio-oil-containing tire with a reduced carbon footprint. The method comprises incorporating about 5 to about 100 phr of bio-oil produced by a recombinant cell into at least one rubber, at least one reinforcing filler, and a cure package, thereby forming an oil-containing rubber composition, and incorporating the oil-containing rubber composition into at least one component of a tire, thereby producing a reduced carbon footprint oil containing tire.

In a third embodiment, a bio-oil-containing rubber composition is disclosed. The composition comprises about 5 to about 100 phr of bio-oil produced by a recombinant cell, at least one rubber, at least one reinforcing filler, and a cure package.

DETAILED DESCRIPTION

The present disclosure relates to rubber compositions comprising bio-oil produced by a recombinant cell. The disclosure also relates to methods of controlling the variability of fatty acid content in bio-oil containing rubber compositions or tires comprising at least one component incorporating the bio-oil containing rubber composition, and to a method of providing a bio-oil-containing tire with a reduced carbon footprint.

In a first embodiment, a method is disclosed for controlling the variability of fatty acid content in a bio-oil-containing rubber composition. The method comprises incorporating about 5 to about 100 phr of bio-oil produced by a recombinant cell with at least one rubber, at least one reinforcing filler, and a cure package, thereby forming a bio-oil-containing rubber composition.

In a second embodiment, a method is disclosed for providing a bio-oil-containing tire with a reduced carbon footprint. The method comprises incorporating about 5 to about 100 phr of bio-oil produced by a recombinant cell into at least one rubber, at least one reinforcing filler, and a cure package, thereby forming an oil-containing rubber composition, and incorporating the oil-containing rubber composition into at least one component of a tire, thereby producing a reduced carbon footprint oil containing tire.

In a third embodiment, a bio-oil-containing rubber composition is disclosed. The composition comprises about 5 to about 100 phr of bio-oil produced by a recombinant cell, at least one rubber, at least one reinforcing filler, and a cure package.

Definitions

The terminology as set forth herein is for description of the embodiments only and should not be construed as limiting the invention as a whole.

As used herein, the term "majority" means at least 51% by weight.

As used herein, the term "minority" means less than 50% by weight.

As used herein, the term "phr" means the parts by weight of rubber. If the rubber composition comprises more than one rubber, "phr" means the parts by weight per hundred parts of the sum of all rubbers.

As used herein, the term "polybutadiene" is used to indicate a polymer that is manufactured from cis-1,3-butadiene monomers. The term polybutadiene is also used interchangeably with the phrase "polybutadiene rubber" and the abbreviation "BR."

As used herein, the term "polyisoprene" means synthetic polyisoprene. In other words, the term is used to indicate a polymer that is manufactured from isoprene monomers, and should not be construed as including naturally occurring natural rubber (e.g., Hevea natural rubber, guayule-sourced natural rubber or dandelion-sourced natural rubber). The term polyisoprene is also used interchangeably with the phrase "polyisoprene rubber" and the abbreviation "IR."

As used herein, the term "styrene-butadiene rubber" or "SBR" means a copolymer manufactured from styrene and cis-1,3-butadiene monomers.

As used herein, the term "natural rubber" or "NR" means naturally occurring rubber such as can be harvested from sources such as Hevea rubber trees, and non-Hevea source (e.g., guayule shrubs, and dandelions (e.g., TKS)). In other words, the term "natural rubber" should not be construed as including polyisoprene.

For the purpose of this disclosure, any reference to a percent amount of a component in the rubber composition means a percent by weight, unless otherwise specified. Similarly, any reference to ratios of component amounts in the rubber composition means the ratios by weight, unless otherwise specified. Unless stated to the contrary, discussions herein relating to the components and amounts of the rubber compositions of the present disclosure should be understood to apply equally to the other embodiments, e.g., the related methods and the tires (and tire treads) containing the rubber compositions disclosed herein.

Bio-Oil Produced by a Recombinant Cell

As discussed above, according to the first-third embodiments disclosed herein, the rubber composition comprises a bio-oil produced by a recombinant cell. In certain embodiments, the recombinant cell comprises an algal cell. The use of bio-oil produced by a recombinant cell offers an alternative to traditional bio-oils which are extracted from plants (e.g., sunflower seeds, coconut, soybeans, etc.). Bio-oils produced by recombinant cells can be produced using a select strain of algal cells which are fed with a supply of sugars (e.g., sucrose) and then allowed to ferment and produce a bio-oil with a selected profile. After sufficient growth or fermentation has taken place, the bio-oil is isolated from the cells and collected. Exemplary bio-oils produced by a recombinant cell are available from Solazyme, Inc. (South San Francisco, California). Exemplary methods for producing bio-oils produced by a recombinant cell are disclosed in U.S. Pat. Nos. 7,935,515; 8,187,860; 8,278,090; 8,476,059; 8,512,999; 8,518,689; 8,580,540; 8,592,188; 8,633,012; 8,697,427; 8,765,424; 8,822,177; 8,822,176; 8,846,375; and 8,889,401, each of which is incorporated by reference herein.

In certain embodiments, the bio-oil produced by a recombinant cell comprises an oil having an oleic acid content of at least about 70% and a linoleic acid content of at least about 5%; including an oleic acid content of at least 70% and a linoleic acid content of at least 5%; an oleic acid content of at least about 75% and a linoleic acid content of at least about 6%, an oleic acid content of at least 75% and a linoleic acid content of at least 6%; an oleic acid content of at least about 80% and a linoleic acid content of at least about 7%, and an oleic acid content of at least 80% and a linoleic acid content of at least 7%.

In certain embodiments, the bio-oil produced by a recombinant cell comprises an oil having either at least 50% of its carbons as naphthenic carbons or at least 50% of its carbons as paraffinic carbons. Standard methods exist for determining the type of carbon content (i.e., aromatic, paraffinic or naphthenic), including, but not limited to, ASTM D2140-08. In certain embodiments, the bio-oil produced by a recombinant cell comprises an oil having about 50 to about 70% naphthenic carbons, including 50 to 70%, about 50 to about 60%, and 50 to 60% naphthenic carbons. In certain embodiments, the bio-oil produced by a recombinant cell comprises an oil having about 60 to about 75% paraffinic carbons, including 60 to 75%, about 65 to about 70%, and 65 to 70% paraffinic carbons.

In certain embodiments, the bio-oil produced by a recombinant cell comprises an oil having an oleic acid content of at least about 55%, a linoleic acid content of at least about 15%, and an alpha-linoleic acid content of at least about 5%; including an oleic acid content of at least 55%, a linoleic acid content of at least 15%, and an alpha-linoleic acid content of at least 5%; an oleic acid content of at least about 65%, a linoleic acid content of at least about 20%, and an alpha-linoleic acid content of at least about 8%; and an oleic acid content of at least 65%, a linoleic acid content of at least 20%, and an alpha-linoleic acid content of at least 8%. In certain embodiments, the bio-oil produced by a recombinant cell comprises an oil having an oleic acid content of about 55% to about 90% and an alpha-linoleic acid content of about 5% to about 15%; including 55% to 90% oleic acid and an alpha-linoleic acid content of 5% to 15%; about 60% to about 85% oleic acid and an alpha-linoleic acid content of about 5% to about 15%; 60% to 85% oleic acid and an alpha-linoleic acid content of 5% to 15%; about 65% to about 85% oleic acid and an alpha-linoleic acid content of about 8% to about 15%; and 65% to 85% oleic acid and an alpha-linoleic acid content of 8% to 15%.

In certain embodiments, the bio-oil produced by a recombinant cell comprises an oil having a lauric acid content of at least about 40%, a myristic acid content of at least about 10%, and a palmitic acid content of at least about 5%; including a lauric acid content of at least 40%, a myristic acid content of at least 10%, and a palmitic acid content of at least 5%; including a lauric acid content of at least about 45%, a myristic acid content of at least about 15%, and a palmitic acid content of at least about 8%; including a lauric acid content of at least 45%, a myristic acid content of at least 15%, and a palmitic acid content of at least 8%. In certain embodiments, the bio-oil produced by a recombinant cell comprises an oil having a lauric acid content of about 40% to about 55%, a myristic acid content of about 10% to about 25%, and a palmitic acid content of about 5% to about 15%; including a lauric acid content of 40% to 55%, a myristic acid content of 10% to 25%, and a palmitic acid content of 5% to 15%; a lauric acid content of about 45% to about 55%, a myristic acid content of about 15% to about 25%, and a palmitic acid content of about 8% to about 15%; and a lauric acid content of 45% to 55%, a myristic acid content of 15% to 25%, and a palmitic acid content of 8% to 15%

In certain embodiments, the bio-oil produced by a recombinant cell comprises an oil having a palmitic acid content of at least about 40%, an oleic acid content of at least about 30%, and a linoleic acid content of at least about 5%; including a palmitic acid content of at least 40%, an oleic acid content of at least 30%, and a linoleic acid content of at least 5%; a palmitic acid content of at least about 45%, an oleic acid content of at least about 35%, and a linoleic acid content of at least about 8%; and a palmitic acid content of at least 45%, an oleic acid content of at least 35%, and a linoleic acid content of at least 8%. In certain embodiments, the bio-oil produced by a recombinant cell comprises an oil having a palmitic acid content of about 40% to about 55%, an oleic acid content of about 30% to about 50%, and a linoleic acid content of about 5% to about 15%; including a palmitic acid content of 40% to 55%, an oleic acid content of 30% to 50%, and a linoleic acid content of 5% to 15%; a palmitic acid content of about 45% to about 55%, an oleic acid content of about 35% to about 45%, and a linoleic acid content of about 8% to about 15%; and a palmitic acid content of 45% to 55%, an oleic acid content of 35% to 45%, and a linoleic acid content of 8% to 15%.

In certain embodiments, the bio-oil produced by a recombinant cell comprises an oil having an oleic acid content of at least about 15%, a linoleic acid content of at least about 45%, an alpha-linoleic acid content of at least about 3%, and a palmitic acid content of at least about 5%; including an oleic acid content of at least 15%, a linoleic acid content of at least 45%, an alpha-linoleic acid content of at least 3%, and a palmitic acid content of at least 5%; an oleic acid content of at least about 20%, a linoleic acid content of at least about 50%, an alpha-linoleic acid content of at least about 5%, and a palmitic acid content of at least about 9%; and an oleic acid content of at least 20%, a linoleic acid content of at least 50%, an alpha-linoleic acid content of at least 5%, and a palmitic acid content of at least 9%. In certain embodiments, the bio-oil produced by a recombinant cell comprises an oil having an oleic acid content of about 15% to about 30%, a linoleic acid content of about 45% to about 65%, an alpha-linoleic acid content of about 3% to about 15%, and a palmitic acid content of about 5% to about 20%; including an oleic acid content of 15% to 30%, a linoleic acid content of 45% to 65%, an alpha-linoleic acid content of 3% to 15%, and a palmitic acid content of 5% to 20%; an oleic acid content of about 20% to about 30%, a linoleic acid content of about 45% to about 65%, an alpha-linoleic acid content of about 5% to about 12%, and a palmitic acid content of about 9% to about 15%; and an oleic acid content of 20% to 30%, a linoleic acid content of 45% to 65%, an alpha-linoleic acid content of 5% to 12%, and a palmitic acid content of 9% to 15%.

In certain embodiments, the bio-oil produced by a recombinant cell comprises an oil having a linoleic acid content of at least about 60% and an oleic acid content of at least about 8%; including a linoleic acid content of at least 60% and an oleic acid content of at least 8%; a linoleic acid content of at least about 65% and an oleic acid content of at least about 10%; and a linoleic acid content of at least 65% and an oleic acid content of at least 10%. In certain embodiments, the bio-oil produced by a recombinant cell comprises an oil having a linoleic acid of about 60% to about 85% linoleic acid and about 8% to about 20% oleic acid; including 60% to 85% linoleic acid and 8% to 20% oleic acid; about 65% to about 85% linoleic acid and about 10% to about 20% oleic acid; including 60% to 85% linoleic acid and 8% to 20% oleic acid; and 65% to 85% linoleic acid and 10% to 20% oleic acid.

As discussed above, according to the first-third embodiments disclosed herein, the rubber composition comprises about 1 to about 200 phr of bio-oil produced by a recombinant cell. It should be understood that in certain such embodiments, the rubber composition comprises one bio-oil produced by a recombinant cell and in other embodiments more than one bio-oil produced by a recombinant cell (i.e., two, three, or more), and that the amounts referred to herein refer to total amounts of all bio-oil produced by a recombinant cell. In certain embodiments of the first-third embodiments, the rubber composition comprises about 5 to about 100 phr of bio-oil produced by a recombinant cell, including 5 to 100 phr, about 5 to about 90 phr, 5 to 90 phr, about 5 to about 80 phr, 5 to 80 phr, about 5 to about 70 phr, 5 to 70 phr, about 5 to about 60 phr, 5 to 60 phr, about 5 to about 50 phr, 5 to 50 phr, about 5 to about 40 phr, 5 to 40 phr, about 10 to about 100 phr, 10 to 100 phr, about 20 to about 100 phr, 20 to 100 phr, about 30 to about 100 phr, 30 to 100 phr, about 40 to about 100 phr, and 40 to 100 phr.

Rubbers

As discussed above, according to the first-third embodiments disclosed herein, the rubber composition comprises at least one rubber. These rubber compositions can be understood as comprising 100 parts of rubber (100 phr), which includes at least one rubber. The at least one rubber can be selected from natural rubber, synthetic rubber, or combinations thereof. Suitable rubbers for use in the rubber composition are well known to those skilled in the art and include, but are not limited to the following: synthetic polyisoprene rubber, natural rubber, styrene-butadiene rubber (SBR), styrene-isoprene rubber, butadiene-isoprene-rubber, styrene-isoprene-butadiene rubber, polybutadiene, butyl rubber (both halogenated and non-halogenated), neoprene (polychloroprene), ethylene-propylene rubber, ethylene-propylene-diene rubber (EPDM), acrylonitrile-butadiene rubber (NBR), silicone rubber, fluorinated rubber, polyacrylate rubber (copolymer of acrylate monomer and vinyl ether), ethylene acrylic rubber, ethylene vinyl acetate copolymer (EVA), epichlorohydrin rubbers, chlorinated polyethylene rubbers, chlorosulfonated polyethylene rubbers, nitrile rubber, halogenated nitrile rubber, hydrogenated nitrile rubber, and tetrafluoroethylene-propylene rubber, and combinations thereof. Examples of fluorinated rubber include perfluoroelastomer rubber, fluoroelastomer, fluorosilicone, and tetrafluoroethylene-propylene rubber.

In certain embodiments of the first-third embodiments disclosed herein, at least a majority (by weight) of the at least one rubber comprises at least one of: natural rubber, polyisoprene rubber, polybutadiene rubber, and styrene-butadiene rubber; in such embodiments, one or more than one type of any of the foregoing rubbers can be utilized. In certain embodiments, at least 60% by weight (at least 60 phr), at least 70% by weight (at least 70 phr), at least 80% by weight (at least 80 phr), at least 90% by weight (at least 90 phr), at least 95% by weight (at least 95 phr), or even 100% by weight (100 phr) of the rubber comprises at least one of: natural rubber, synthetic polyisoprene rubber, polybutadiene rubber, and styrene-butadiene rubber.

In certain embodiments of the first-third embodiments disclosed herein, a minority (by weight) of the at least one rubber comprises at least one of: styrene-isoprene rubber, butadiene-isoprene-rubber, styrene-isoprene-butadiene rubber, butyl rubber (both halogenated and non-halogenated), neoprene (polychloroprene), ethylene-propylene rubber, ethylene-propylene-diene rubber (EPDM), acrylonitrile-butadiene rubber (NBR), silicone rubber, fluorinated rubber, polyacrylate rubber (copolymer of acrylate monomer and vinyl ether), ethylene acrylic rubber, ethylene vinyl acetate copolymer (EVA), epichlorohydrin rubbers, chlorinated polyethylene rubbers, chlorosulfonated polyethylene rubbers, nitrile rubber, halogenated nitrile rubber, hydrogenated nitrile rubber, and tetrafluoroethylene-propylene rubber. In certain embodiments, up to 40% by weight (up to 40 phr), up to 30% by weight (up to 30 phr), up to 20% by weight (up to 20 phr), up to 10% by weight (up to 10 phr), up to 5% by weight (up to 5 phr) of the rubber comprises at least one of: styrene-isoprene rubber, butadiene-isoprene-rubber, styrene-isoprene-butadiene rubber, butyl rubber (both halogenated and non-halogenated), neoprene (polychloroprene), ethylene-propylene rubber, ethylene-propylene-diene rubber (EPDM), acrylonitrile-butadiene rubber (NBR), silicone rubber, fluorinated rubber, polyacrylate rubber (copolymer of acrylate monomer and vinyl ether), ethylene acrylic rubber, ethylene vinyl acetate copolymer (EVA), epichlorohydrin rubbers, chlorinated polyethylene rubbers, chlorosulfonated polyethylene rubbers, nitrile rubber, halogenated nitrile rubber, hydrogenated nitrile rubber, and tetrafluoroethylene-propylene rubber. In other embodiments, 0% by weight (0 phr) of the rubber comprises styrene-isoprene rubber, butadiene-isoprene-rubber, styrene-isoprene-butadiene rubber, butyl rubber (both halogenated and non-halogenated), neoprene (polychloroprene), ethylene-propylene rubber, ethylene-propylene-diene rubber (EPDM), acrylonitrile-butadiene rubber (NBR), silicone rubber, fluorinated rubber, polyacrylate rubber (copolymer of acrylate monomer and vinyl ether), ethylene acrylic rubber, ethylene vinyl acetate copolymer (EVA), epichlorohydrin rubbers, chlorinated polyethylene rubbers, chlorosulfonated polyethylene rubbers, nitrile rubber, halogenated nitrile rubber, hydrogenated nitrile rubber, and tetrafluoroethylene-propylene rubber; in certain such embodiments, 100 phr of the rubber comprises at least one of: natural rubber, synthetic polyisoprene rubber, polybutadiene rubber, and styrene-butadiene rubber. In yet other embodiments, up to 100% by weight (100 phr), including up to 90% by weight (90 phr), up to 80% by weight (80 phr), up to 70% by weight (70 phr) and up to 60% by weight (60 phr) of the rubber comprises at least one of: styrene-isoprene rubber, butadiene-isoprene-rubber, styrene-isoprene-butadiene rubber, butyl rubber (both halogenated and non-halogenated), neoprene (polychloroprene), ethylene-propylene rubber, ethylene-propylene-diene rubber (EPDM), acrylonitrile-butadiene rubber (NBR), silicone rubber, fluorinated rubber, polyacrylate rubber (copolymer of acrylate monomer and vinyl ether), ethylene acrylic rubber, ethylene vinyl acetate copolymer (EVA), epichlorohydrin rubbers, chlorinated polyethylene rubbers, chlorosulfonated polyethylene rubbers, nitrile rubber, halogenated nitrile rubber, hydrogenated nitrile rubber, and tetrafluoroethylene-propylene rubber.

In certain embodiments of the first-third embodiments disclosed herein, the at least one rubber comprises a polymer, a copolymer, or a combination thereof (i.e., more than one polymer, more than one copolymer, one polymer and one copolymer, more than one polymer and one copolymer, more than one copolymer and one polymer, or more than one copolymer and more than one polymer) when more than one rubber is utilized. In certain embodiments of the first-third embodiments disclosed herein, the at least one rubber includes at least one diene monomer-containing polymer or copolymer. Examples of suitable diene monomers according to certain embodiments of the first-third embodiments disclosed herein include, but are not limited to, 1,3-butadiene, isoprene, 1,3-pentadiene, 1,3-hexadiene, 2,3-dimethyl-1,3-butadiene, 2-ethyl-1,3-butadiene, 2-methyl-1,3-pentadiene, 3-methyl-1,3-pentadiene, 4-methyl-1,3-pentadiene, 2,4-hexadiene, 1,3-cyclopentadiene, 1,3-cyclohexadiene, 1,3-cycloheptadiene, and 1,3-cyclooctadiene, and derivatives thereof. It should be understood that mixtures of two or more dienes may be utilized in certain embodiments. Non-limiting examples of suitable polymers that are diene monomer-containing polymers or copolymers include, but are not limited to, styrene-butadiene rubber, polybutadiene, polyisoprene, styrene-isoprene rubber, styrene-butadiene-isoprene rubber, and natural rubber. In certain embodiments of the first-third embodiments disclosed herein, the at least one rubber is at least one of: styrene-butadiene rubber, polybutadiene, synthetic polyisoprene rubber, and natural rubber.

As discussed above, in certain embodiments according to the first-third embodiments, the at least one rubber comprises polybutadiene. In certain embodiments according to the first-third embodiments, the polybutadiene comprises a high cis polybutadiene. In certain embodiments according to the first-third embodiments, the high cis polybutadiene has a cis 1,4-bond content of 85% of greater, 90% or greater, 92% or greater, or 95% or greater. In certain embodiments of the first-third embodiments, the polybutadiene has a cis 1,4-bond content of 85-99%, 90-99%, 90-98%, 90-97%, 92-99%, 92-98%, 92-97%, 95-99%, 95-98%, or 95-97%. In certain embodiments according to the first-third embodiments, the polybutadiene comprises a low cis polybutadiene. In certain embodiments according to the first-third embodiments, the polybutadiene comprises a low cis polybutadiene. In certain embodiments according to the first-third embodiments, the low polybutadiene has a cis 1,4-bond content of less than 50%, less than 45%, or less than 40%.

Generally, various polymerization methods are known for producing polybutadiene having a cis 1,4-bond content of 85% or greater, 90% or greater, 92% or greater, or 95% or greater and it should be understood that the particular method by which the polybutadiene is produced is not limited as long as the resulting polybutadiene has the specified cis 1,4-bond content. The percentages are based upon the number of diene mer units adopting the cis-1,4 linkage versus the total number of diene mer units. Polymerization of high-cis 1,4-polybutadiene is described in U.S. Pat. Nos. 3,297,667, 3,541,063, 3,794,604, 4,461,883, 4,444,903, 4,525,594, 4,699,960, 5,017,539, 5,428,119, 5,064,910, and 5,844,050, 7,094,849, all of which are hereby incorporated by reference. Exemplary polymerization methods include, but are not limited to, those employing Ziegler-Natta catalysts based on transition metals (e.g., lanthanides such as neodymium), nickel catalysts and titanium-based catalysts as well as solution, emulsion and bulk polymerization processes. Generally, the cis 1,4-, vinyl 1,2-, and trans 1,4-bond linkage contents in a given polymer such as polybutadiene can be determined by standard and well-established analytical methods such as infrared spectroscopy.

As discussed above, in certain embodiments according to the first-third embodiments, the at least one rubber comprises polyisoprene. In certain embodiments according to the first-third embodiments, the polyisoprene comprises high cis polyisoprene. In certain embodiments according to the first-third embodiments, the high cis polyisoprene has a cis 1,4-bond content of 90% of greater. In certain embodiments of the first-third embodiments, the polyisoprene has a cis 1,4-bond content of 90% or greater, 92% or greater, or 95% or greater. In certain embodiments of the first-third embodiments, the polyisoprene has a cis 1,4-bond content of 90-99%, 90-98%, 90-97%, 92-99%, 92-98%, 92-97%, 95-99%, 95-98%, or 95-97%.

Generally, various polymerization methods are known for producing polyisoprene, including polyisoprene having a cis 1,4-bond content of 90% or greater, and it should be understood that the particular method by which the polyisoprene is produced is not limited as long as the resulting polymer has the desired cis 1,4-bond content. As previously discussed with respect to polybutadiene, the percentages are based upon the number of diene mer units adopting the cis-1,4 linkage versus the total number of diene mer units. Polymerization of high-cis polyisoprene is described in U.S. Pat. Nos. 8,664,343; 8,188,201; 7,008,899; 6,897,270; and 6,699,813, all of which are hereby incorporated by reference. Exemplary polymerization methods include, but are not limited to, those employing Ziegler-Natta catalyst systems and those employing anionic polymerization with organometallic catalysts such as alkyl lithium in hydrocarbon solvents. As previously discussed with respect to polybutadiene, the cis-1,4-, cis-1,2-, and trans-1,4-linkage contents in a given polymer such as polyisoprene can be determined by standard and well-established analytical methods such as infrared spectroscopy.

As discussed above, in certain embodiments according to the first-third embodiments, the at least one rubber comprises the copolymer styrene-butadiene rubber (SBR). SBR is a copolymer of styrene and butadiene monomers. In certain embodiments according to the first-third embodiments disclosed herein, the SBR used in the rubber composition comprises about 10 to about 50% styrene monomer and about 50 to about 90% butadiene monomer by weight. In certain embodiments according to the first-third embodiments disclosed herein, the SBR used in the rubber composition comprises 10 to 50% styrene monomer and 50 to 90% butadiene monomer by weight. Generally, SBR is produced by solution or emulsion polymerization methods; however, it should be understood that the particular method by which the SBR is produced is not limited. The styrene and butadiene monomer content in a given SBR copolymer can be determined by standard and well-established analytical methods such as infrared spectroscopy.

Numerous commercial sources of the foregoing rubbers are well-known. As non-limiting examples, Firestone Polymers offers various grades of its Diene™ polybutadiene which have varying cis 1,4-bond contents (e.g., 40% and 96%) as well as various grades of its Duradene™ solution polymerized styrene-butadiene copolymer. Other commercial sources of the rubbers are well known, including sources for emulsion polymerized styrene-butadiene copolymer, functionalized versions of styrene-butadiene copolymer, neoprene, polybutadiene, synthetic polyisoprene rubber, and natural rubber.

In certain embodiments according to the first-third embodiments disclosed herein, the at least one rubber of the rubber composition comprises a functionalized polymer. In certain such embodiments, the rubber composition comprises about 5 to about 100 phr of at least one functionalized polymer, including 5 phr to 100 phr, about 10 to about 90 phr, 10 phr to 90 phr, about 10 to about 70 phr, 10 phr to 70 phr, about 10 to about 50 phr, and 10 phr to 50 phr. In certain embodiments according to the first-third embodiments disclosed herein, the functionalized polymer comprises a polymer with a silica-reactive functional group, a nitrogen-containing functional group, an oxygen-containing functional group, a sulfur-containing functional group, or a combination of the foregoing. Non-limiting examples of silica-reactive functional groups that are known to be utilized in functionalizing conjugated diene polymers and are suitable for use in the rubber compositions of certain embodiments of the first-third embodiments disclosed herein include nitrogen-containing functional groups, silicon-containing functional groups, oxygen or sulfur-containing functional groups, and metal-containing functional groups. As used herein, the term functionalized polymer should be understood to include polymers (including conjugated diene monomer-containing polymer or copolymer rubbers) with a functional group at one or both terminus (e.g., from use of a functionalized initiator, a functionalized terminator, or both), a functional group in the main chain of the polymer, and combinations thereof. For example, a silica-reactive functionalized polymer may have the functional group at one or both terminus, in the main chain thereof, or both in the main chain and at one or both terminus.

Non-limiting examples of nitrogen-containing functional groups that are known to be utilized in functionalizing rubbers include, but are not limited to, any of a substituted or unsubstituted amino group, an amide residue, an isocyanate group, an imidazolyl group, an indolyl group, a nitrile group, a pyridyl group, and a ketimine group. The foregoing substituted or unsubstituted amino group should be understood to include a primary alkylamine, a secondary alkylamine, or a cyclic amine, and an amino group derived from a substituted or unsubstituted imine. In certain embodiments according to the first-third embodiments disclosed herein, the rubber composition comprises a functionalized conjugated diene monomer-containing polymer or copolymer rubber having at least one functional group selected from the foregoing list.

Non-limiting examples of silicon-containing functional groups that are known to be utilized in functionalizing rubbers include, but are not limited to, an organic silyl or siloxy group, and more precisely, the functional group may be selected from an alkoxysilyl group, an alkylhalosilyl group, a siloxy group, an alkylaminosilyl group, and an alkoxyhalosilyl group. Suitable silicon-containing functional groups for use in functionalizing rubbers also include those disclosed in U.S. Pat. No. 6,369,167, the entire disclosure of which is hereby incorporated by reference. In certain embodiments according to the first-third embodiments disclosed herein, the rubber composition comprises a functionalized rubber having at least one functional group selected from the foregoing list.

Non-limiting examples of oxygen or sulfur-containing functional groups that are known to be utilized in functionalizing rubbers include, but are not limited to, a hydroxyl group, a carboxyl group, an epoxy group, a glycidoxy group, a diglycidylamino group, a cyclic dithiane-derived functional group, an ester group, an aldehyde group, an alkoxy group, a ketone group, a thiocarboxyl group, a thioepoxy group, a thioglycidoxy group, a thiodiglycidylamino group, a thioester group, a thioaldehyde group, a thioalkoxy group and a thioketone group. In certain embodiments, the foregoing alkoxy group may be an alcohol-derived alkoxy group derived from a benzophenone. In certain embodiments according to the first-third embodiments disclosed herein, the rubber composition comprises a functionalized diene monomer-containing polymer or copolymer rubber having at least one functional group selected from the foregoing list.

Generally, rubbers, including diene monomer-containing polymer or copolymer rubbers, may be prepared and recovered according to various suitable methods such as batch, semi-continuous, or continuous operations, as are well known to those having skill in the art. The polymerization can also be carried out in a number of different polymerization reactor systems, including but not limited to bulk polymerization, vapor phase polymerization, solution polymerization, suspension polymerization, coordination polymerization, and emulsion polymerization. The polymerization may be carried out using a free radical mechanism, an anionic mechanism, a cationic mechanism, or a coordination mechanism. All of the above polymerization methods are well known to persons skilled in the art. However, for exemplary purposes, a short description of polymerization via an anionic mechanism is given.

When rubbers, such as diene monomer-containing polymer or copolymer rubbers, are produced through anionic polymerization, an organic alkaline metal compound, preferably a lithium-containing compound, is typically used as a polymerization initiator. Examples of lithium-containing compounds used as polymerization initiators include, but are not limited to, hydrocarbyl lithium compounds, lithium amide compounds, and similar lithium compounds. The amount of the lithium compound used as the polymerization initiator is preferably within a range of 0.2 to 20 millimoles per 100 g of the monomer.

Non-limiting examples of hydrocarbyl lithium compounds include ethyl lithium, n-propyl lithium, isopropyl lithium, n-butyl lithium, sec-butyl lithium, tert-octyl lithium, n-decyl lithium, phenyl lithium, 2-naphthyl lithium, 2-butylphenyl lithium, 4-phenyl-butyl lithium, cyclohexyl lithium, cyclopentyl lithium, a reaction product of diisopropenylbenzene and butyl lithium, and mixtures thereof. Among these, alkyl lithium compounds such as ethyl lithium, n-propyl lithium, isopropyl lithium, n-butyl lithium, sec-butyl lithium, tert-octyl lithium, n-decyl lithium and so on are preferable, and n-butyl lithium is particularly preferable.

Methods for producing rubbers, such as diene-monomer-containing polymer or copolymer rubbers, through anionic polymerization using an organic alkaline metal compound as the polymerization initiator are not particularly limited. For example, a diene monomer-containing polymer or copolymer rubber can be produced by polymerizing a conjugated diene monomer alone or a mixture of a diene monomer and aromatic vinyl compound in a hydrocarbon solvent inactive to the polymerization reaction. Non-limiting examples of the hydrocarbon solvent inactive to the polymerization reaction include propane, n-butane, isobutane, n-pentane, isopentane, n-hexane, cyclohexane, propene, 1-butene, isobutene, trans-2-butene, cis-2-butene, 1-pentene, 2-pentene, 1-hexene, 2-hexene, benzene, toluene, xylene, ethylbenzene and mixtures thereof.

The anionic polymerization may be carried out in the presence of a randomizer. The randomizer can control the microstructure of the diene compound, and has an action that the 1,2-bond content in butadiene unit of the polymer using, for example, butadiene as a monomer is controlled, and butadiene unit and styrene unit in the copolymer using butadiene and styrene as a monomer are randomized, or the like. Non-limiting examples of the randomizer include dimethoxybenzene, tetrahydrofuran, dimethoxyethane, diethylene glycol dibutyl ether, diethylene glycol dimethyl ether, bis tetrahydrofuryl propane, triethylamine, pyridine, N-methylmorpholine, N,N,N',N'-tetramethyl ethylenediamine, 1,2-dipiperidinoethane, potassium-t-amylate, potassium-1-butoxide, sodium-1-amylate and so on. The amount of the randomizer used is preferably within a range of 0.01 to 100 molar equivalents per 1 mol of the organic alkaline metal compound as a polymerization initiator.

The anionic polymerization may be carried out through any of solution polymerization, vapor phase polymerization and bulk polymerization. In the solution polymerization, the concentration of the monomer in the solution is preferably within a range of 5 to 50% by mass, more preferably 10 to 30% by mass. When the conjugated diene monomer and a vinyl aromatic monomer are used together, the content of the vinyl aromatic monomer in the mixture is preferably within a range of 3 to 50% by mass, more preferably 4 to 45% by mass. Also, the polymerization system is not particularly limited and may be a batch system or a continuous system.

The polymerization temperature in the anionic polymerization is preferably within a range of 0 to 150° C., more preferably 20 to 130° C. The polymerization may be carried out under a generating pressure or, preferably, at a pressure sufficient to keep the reaction monomers substantially in a liquid phase. When the polymerization reaction is carried out under a pressure higher than the generating pressure, the reaction system is preferably pressurized with an inert gas. Preferably, any reaction-obstructing substances, such as water, oxygen, carbon dioxide, protonic compounds, and the like are removed before beginning the polymerization reaction.

Typically, in the rubber compositions according to the first-third embodiments disclosed herein, the overall composition contains 100 phr (in total) of at least one rubber. In other words, the total amount of all rubbers is considered to be 100 parts (by weight) and denoted 100 phr. Other components are added based upon 100 parts (in total) of rubber(s). As a non-limiting example, 60 parts of styrene-butadiene copolymer could be utilized along with 40 parts of polybutadiene polymer and 60 parts of silica; these amounts would be described herein as 60 phr of styrene-butadiene copolymer, 40 phr of polybutadiene polymer and 60 phr of silica.

Oil-Extended Rubbers

Also disclosed herein, is an oil-extended rubber comprising at least one rubber and about 5 to about 50 phr (including 5 to 50 phr) of a bio-oil produced by a recombinant cell. In certain embodiment of the foregoing, the oil-extended rubber comprises about 5 to about 45 phr of a bio-oil produced by a recombinant cell, including 5 to 45 phr, about 5 to about 40 phr, and 5 to 40 phr. The rubber in the oil-extended rubber may comprise any of the rubber discussed above. In certain embodiments, the at least one rubber of the oil-extended rubber comprises at least one diene monomer-containing polymer or copolymer; in certain such embodiments, the at least one diene-monomer-containing polymer or copolymer comprises at least one of polybutadiene, styrene-butadiene copolymer, natural rubber, or polyisoprene.

Reinforcing Filler(s)

As discussed above, according to the first-third embodiments disclosed herein, the rubber composition comprises about 5 to about 200 phr of at least one reinforcing filler. One or more than one reinforcing filler may be utilized in the rubber compositions according to the first-third embodiments disclosed herein. In certain embodiments of the first-third embodiments disclosed herein, the total amount of the reinforcing filler is 5 to 200 phr, including about 10 to about 200 phr, 10 to 200 phr, about 10 to about 175 phr, 10 to 175 phr, about 25 to about 150 phr. 25 to 150 phr, about 35 to about 150 phr, 35 to 150 phr, about 25 to about 125 phr, 25 to 125 phr, about 25 to about 100 phr, 25 to 100 phr, about 25 to about 80 phr, 25 to 80 phr, about 35 to about 125 phr, 35 to 125 phr, about 35 to about 100 phr, 35 to 100 phr, about 35 to about 80 phr, and 35 to 80 phr of at least one reinforcing filler. In certain embodiments, the useful upper range for the amount of reinforcing filler can be considered to be somewhat limited by the high viscosity imparted by fillers of this type.

As used herein, the term "reinforcing" with respect to "reinforcing carbon black filler," "reinforcing silica filler," and "reinforcing fillers" generally should be understood to encompass both fillers that are traditionally described as reinforcing as well as fillers that may traditionally be described as semi-reinforcing. Traditionally, the term "reinforcing filler" is used to refer to a particulate material that has a nitrogen absorption specific surface area (N2SA) of more than about 100 $m^2/g$, and in certain instances more than 100 $m^2/g$, more than about 125 $m^2/g$, more than 125 $m^2/g$, or even more than about 150 $m^2/g$ or more than 150 $m^2/g$. Alternatively, the traditional use of the term "reinforcing filler" can also be used to refer to a particulate material that has a particle size of about 10 nm to about 50 nm (including 10 nm to 50 nm). Traditionally, the term "semi-reinforcing filler" is used to refer to a filler that is intermediary in either particle size, surface area (N2SA), or both, to a non-reinforcing filler and a reinforcing filler. In certain embodiments of the first-third embodiments disclosed herein, the term "reinforcing filler" is used to refer to a particulate material that has a nitrogen absorption specific surface area (N2SA) of about 20 m²/g or greater, including 20 m²/g or greater, more than about 50 m²/g, more than 50 m²/g, more than about 100 m²/g, more than 100 m²/g, more than about 125 m²/g, and more than 125 m²/g. In certain embodiments of the first-third embodiments disclosed herein, the term "reinforcing filler" is used to refer to a particulate material that has a particle size of about 10 nm up to about 1000 nm, including 10 nm to 1000 nm, about 10 nm up to about 50 nm and 10 nm to 50 nm.

In certain embodiments of the first-third embodiments disclosed herein, the at least one reinforcing filler comprises at least one of: carbon black or silica. In other words, in such embodiments, the at least one reinforcing filler comprises at least one carbon black, at least one silica, or at least one carbon black and at least one silica. In certain embodiments of the first-third embodiments disclosed herein, the at least one reinforcing filler comprises at least one of: carbon black or silica, and further comprises at least one additional reinforcing filler. In other words, in such embodiments, the at least one reinforcing filler comprises at least one carbon black and at least one additional reinforcing filler (other than silica), at least one silica and at least one additional reinforcing filler (other than carbon black), or at least one silica and at least one carbon black and at least one additional reinforcing filler (other than the carbon black or silica). As discussed in more detail below, in certain embodiments of the first-third embodiments disclosed herein, the at least one reinforcing filler comprises at least one reinforcing filler other than carbon black or silica.

Silica

As discussed above, in certain embodiments of the first-third embodiments disclosed herein the rubber composition comprises at least one reinforcing filler which comprises silica. Suitable reinforcing silica fillers for use in the rubber composition of certain embodiments of the first-third embodiments disclosed herein are well known. Non-limiting examples of reinforcing silica fillers suitable for use in the rubber compositions of certain embodiments of the first-third embodiments disclosed herein include, but are not limited to, precipitated amorphous silica, wet silica (hydrated silicic acid), dry silica (anhydrous silicic acid), fumed silica, calcium silicate and the like. Other suitable reinforcing silica fillers for use in rubber compositions of certain embodiments of the first-third embodiments disclosed herein include, but are not limited to, aluminum silicate, magnesium silicate ($Mg_2SiO_4$, $MgSiO_3$ etc.), magnesium calcium silicate ($CaMgSiO_4$), calcium silicate ($Ca_2SiO_4$ etc.), aluminum silicate ($Al_2SiO_5$, $Al_4 \cdot 3SiO_4 \cdot 5H_2O$ etc.), aluminum calcium silicate ($Al_2O_3 \cdot CaO_2SiO_2$, etc.), and the like. Among the listed reinforcing silica fillers, precipitated amorphous wet-process, hydrated silica fillers are preferred. Such reinforcing silica fillers are produced by a chemical reaction in water, from which they are precipitated as ultrafine, spherical particles, with primary particles strongly associated into aggregates, which in turn combine less strongly into agglomerates. The surface area, as measured by the BET method, is a preferred measurement for characterizing the reinforcing character of different reinforcing silica fillers. In certain embodiments of the first-third embodiments disclosed herein, the rubber composition comprises a reinforcing silica filler having a surface area (as measured by the BET method) of about 32 m²/g to about 400 m²/g (including 32 m²/g to 400 m²/g), with the range of about 100 m²/g to about 300 m²/g (including 100 m²/g to 300 m²/g) being preferred, and the range of about 150 m²/g to about 220 m²/g (including 150 m²/g to 220 m²/g) being included. In certain embodiments of the first-third embodiments disclosed herein, the rubber composition comprises reinforcing silica filler having a pH of about 5.5 to about 7 or slightly over 7, preferably about 5.5 to about 6.8. Some of the commercially available reinforcing silica fillers which can be used in the rubber compositions of certain embodiments of the first-third embodiments disclosed herein include, but are not limited to, Hi-Sil® 190, Hi-Sil®210, Hi-Sil® 215, Hi-Sil®233, Hi-Sil®243, and the like, produced by PPG Industries (Pittsburgh, Pa.). As well, a number of useful commercial grades of different reinforcing silica fillers are also available from Degussa Corporation (e.g., VN2, VN3), Rhone Poulenc (e.g., Zeosil™ 1165MP), and J. M. Huber Corporation.

In certain embodiments of the first-third embodiments disclosed herein, as discussed in more detail below, the reinforcing silica filler comprises a silica that has been pre-treated with a silica coupling agent; preferably the pre-treated silica comprises a silica that has been pre-treated with a silane-containing silica coupling agent.

Carbon Black

As discussed above, in certain embodiments of the first-third embodiments disclosed herein the rubber composition comprises at least one reinforcing filler which comprises silica. As discussed in more detail below, most carbon blacks are commonly understood to be reinforcing fillers. In certain embodiments of the first-third embodiments disclosed herein, the rubber composition comprises carbon black in an amount of from zero to about 50% by weight of the total reinforcing filler, including zero to 50%, about 5% to about 30%, 5% to 30%, from about 5% to about 20%, 5% to 20%, about 10% to about 30%, 10% to 30%, about 10% to about 20%, and 10% to 20% by weight of the total reinforcing filler. In certain embodiments of the first-third embodiments disclosed herein, the carbon black comprises no more than about 30% by weight (including no more than 30% by weight) of the total reinforcing filler in the rubber composition. In certain embodiments of the first-third embodiments disclosed herein, the rubber composition comprises about 5 to about 100 phr (including 5 to 100 phr) of one or more carbon blacks.

Generally, suitable carbon black for use as a reinforcing filler in the rubber composition of certain embodiments of the first-third embodiments disclosed herein includes any of the commonly available, commercially-produced carbon blacks, including those having a surface area of at least about 20 m²/g (including at least 20 m²/g) and, more preferably, at least about 35 m²/g up to about 200 m²/g or higher (including 35 m²/g up to 200 m²/g). Surface area values used in this application are determined by ASTM D-1765 using the cetyltrimethyl-ammonium bromide (CTAB) technique. Among the useful carbon blacks are furnace black, channel blacks, and lamp blacks. More specifically, examples of useful carbon blacks include super abrasion furnace (SAF) blacks, high abrasion furnace (HAF) blacks, fast extrusion furnace (FEF) blacks, fine furnace (FF) blacks, intermediate super abrasion furnace (ISAF) blacks, semi-reinforcing furnace (SRF) blacks, medium processing channel blacks, hard processing channel blacks and conducting channel blacks. Other carbon blacks which can be utilized include acetylene blacks. In certain embodiments of the first-third embodiments disclosed herein, the rubber composition includes a mixture of two or more of the foregoing blacks. Typical suitable carbon blacks for use in certain embodiments of the first-third embodiments disclosed herein are N-110, N-220, N-339, N-330, N-351, N-550, and N-660, as designated by ASTM D-1765-82a.

The carbon blacks utilized can be in pelletized form or an unpelletized flocculent mass. Preferably, for more uniform mixing, unpelletized carbon black is preferred.

Other Fillers

As discussed above, in certain embodiments of the first-third embodiments disclosed herein, the rubber composition comprises at least one reinforcing filler comprising a reinforcing filler other than carbon black or silica. In those embodiments of the first-third embodiments disclosed herein where the rubber composition comprises at least one reinforcing filler comprising silica, carbon black, or both, this reinforcing filler other than carbon black or silica may be referred to as an additional reinforcing filler. In certain embodiments of the first-third embodiments disclosed herein, the rubber composition comprises at least one of: carbon black or silica, and at least one additional reinforcing filler. In other words, in certain embodiments of the first-third embodiments disclosed herein, the rubber composition comprises at least reinforcing carbon black and at least one additional reinforcing filler; at least one reinforcing silica filler and at least one additional reinforcing filler; or at least one reinforcing carbon black, at least one reinforcing silica filler, and at least one additional reinforcing filler.

Suitable reinforcing fillers other than carbon black or silica for use in the rubber composition of certain embodiments of the first-third embodiments disclosed herein are well known. Non-limiting examples of suitable additional reinforcing fillers for use in the rubber compositions of certain embodiments of the first-third embodiments disclosed herein include, but are not limited to, alumina, aluminum hydroxide, clay (reinforcing grades), magnesium hydroxide, boron nitride, aluminum nitride, titanium dioxide, reinforcing zinc oxide, and combinations thereof.

As discussed above, in certain embodiments of the first-third embodiments disclosed herein, the rubber compositions comprises at least one non-reinforcing filler. In certain embodiments of the first-third embodiments disclosed herein, the rubber composition comprises at least one non-reinforcing filler in addition to the at least one reinforcing filler. In other embodiments of the first-third embodiments disclosed herein, the rubber composition comprises at least one non-reinforcing filler without the need for any reinforcing filler, i.e., in such embodiments the at least one non-reinforcing filler is essential while a reinforcing filler is not.

In certain embodiments of the first-third embodiments, the rubber composition further comprises at least one non-reinforcing filler. In certain embodiments, the term "non-reinforcing filler" is used to refer to a particulate material that has a nitrogen absorption specific surface area (N2SA) of less than about 20 m$^2$/g (including less than 20 m$^2$/g), and in certain embodiments less than about 10 m$^2$/g (including less than 10 m$^2$/g). The N2SA surface area of a particulate material can be determined according to various standard methods including ASTM D6556. In certain embodiments of the compositions and methods disclosed herein, the term "non-reinforcing filler" is used to refer to a particulate material that has a particle size of greater than about 1000 nm (including greater than 1000 nm).

Suitable non-reinforcing fillers for use in the rubber composition of certain embodiments of the first-third embodiments disclosed herein are well known. In certain embodiments of the first-third embodiments disclosed herein, the rubber composition further comprises at least one of the following non-reinforcing fillers: clay, graphite, talc, mica, titanium dioxide, magnesium dioxide, aluminum oxide, titanium oxide, calcium oxide, aluminum hydroxide, starch, boron nitride, silicon nitride, aluminum nitride, etc.), silicon carbide, aluminum carbonate ($Al_2(CO_3)_2$, non-reinforcing grades of calcium carbonate ($CaCO_3$), magnesium carbonate ($MgCO_3$), calcium oxide, mica, calcium oxide, boron nitride, silicon nitride, aluminum nitride, calcium silicate (or silicon carbide ($Ca_2SiO_4$, etc.), or crystalline aluminosilicates. In certain embodiments of the first-third embodiments disclosed herein, the rubber composition further comprises a non-reinforcing carbon black. Examples of suitable carbon blacks having a nitrogen surface area of no more than 20 m$^2$/g include, but are not limited to, thermal blacks or the N9 series carbon blacks (also referred to as the N-900 series), such as those with the ASTM designation N-907, N-908, N-990, and N-991. Various carbon blacks meeting the foregoing are commercially available, including but not limited to Thermax® N990 carbon black from Cancarb Limited (Medicine Hat, Alberta, Canada).

In certain embodiments of the first-third embodiments, the rubber composition further comprises at least one inorganic filler (other than silica). Such an inorganic filler can be described as a non-silica inorganic filler. In other words, certain embodiments of the first-third embodiments disclosed herein, the rubber composition comprises at least one inorganic filler (other than silica) in addition to the at least one reinforcing filler. In other embodiments of the first-third embodiments disclosed herein, the rubber composition comprises at least one inorganic filler (other than silica) without the need for any reinforcing filler, i.e., in such embodiments the at least one inorganic filler (other than silica) is essential while a reinforcing filler is not.

Inorganic fillers (other than silica) suitable for use in rubber compositions are well known. In certain embodiments of the first-third embodiments disclosed herein, the rubber composition comprises at one of the following inorganic fillers: aluminum hydroxide, talc, clay, alumina ($Al_2O_3$), aluminum hydrate ($Al_2O_3H_2O$), aluminum hydroxide ($Al(OH)_3$), aluminum carbonate ($Al_2(CO_3)_2$), aluminum nitride, aluminum magnesium oxide ($MgOAl_2O_3$), aluminum silicate ($Al_2SiO_5$, $Al_4·3SiO_4·5H_2O$ etc.), aluminum calcium silicate ($Al_2O_3·CaO_2SiO_2$, etc.), pyrofilite ($Al_2O_34SiO_2·H_2O$), bentonite ($Al_2O_3·4SiO_2·2H_2O$), boron nitride, mica, kaolin, glass balloon, glass beads, calcium oxide (CaO), calcium hydroxide ($Ca(OH)_2$), calcium carbonate ($CaCO_3$), calcium silicate ($Ca_2SiO_4$ etc.), magnesium carbonate, magnesium hydroxide ($MH(OH)_2$), magnesium oxide (MgO), magnesium carbonate ($MgCO_3$), magnesium silicate ($Mg_2SiO_4$, $MgSiO_3$ etc.), magnesium calcium silicate ($CaMgSiO_4$), titanium oxide, titanium dioxide, potassium titanate, barium sulfate, zirconium oxide ($ZrO_2$), zirconium hydroxide [$Zr(OH)_2·nH_2O$], zirconium carbonate [$Zr(CO_3)_2$], crystalline aluminosilicates, reinforcing grades of zinc oxide (i.e., reinforcing zinc oxide), and combinations thereof. In certain embodiments of the first-third embodiments disclosed herein, the rubber composition comprises at least one reinforcing filler (as discussed above) and at least one of the following inorganic fillers: aluminum hydroxide, talc, clay, alumina ($Al_2O_3$), aluminum hydrate ($Al_2O_3H_2O$), aluminum hydroxide ($Al(OH)_3$), aluminum carbonate ($Al_2(CO_3)_2$), aluminum nitride, aluminum magnesium oxide ($MgOAl_2O_3$), aluminum silicate ($Al_2SiO_5$, $Al_4·3SiO_4·5H_2O$ etc.), aluminum calcium silicate ($Al_2O_3·CaO_2SiO_2$, etc.), pyrofilite ($Al_2O_34SiO_2·H_2O$), bentonite ($Al_2O_3·4SiO_2·2H_2O$), boron nitride, mica, kaolin, glass balloon, glass beads, calcium oxide (CaO), calcium hydroxide ($Ca(OH)_2$), calcium carbonate ($CaCO_3$), calcium silicate ($Ca_2SiO_4$ etc.), magnesium carbonate, magnesium hydroxide ($MH(OH)_2$), magnesium oxide (MgO), magnesium carbonate ($MgCO_3$), magnesium silicate ($Mg_2SiO_4$, MgSiO$_3$ etc.), magnesium calcium silicate (CaMgSiO$_4$), titanium oxide, titanium dioxide, potassium titanate, barium sulfate, zirconium oxide (ZrO$_2$), zirconium hydroxide [Zr (OH)$_2$·nH$_2$O], zirconium carbonate [Zr(CO$_3$)$_2$], crystalline aluminosilicates, reinforcing grades of zinc oxide (i.e., reinforcing zinc oxide), and combinations thereof.

Silica Coupling Agents

In certain embodiments of the first-third embodiments disclosed herein, the rubber composition includes one or more silica coupling agents. Silica coupling agents are useful in preventing or reducing aggregation of the silica filler in those rubber compositions of the first-third embodiments that include a silica filler. Aggregates of the silica filler particles are believed to increase the viscosity of the rubber composition, and, therefore, preventing this aggregation reduces the viscosity and improves the processability and blending of the rubber composition.

Generally, any conventional type of silica coupling agent can be used, such as those having a silane and a constituent component or moiety that can react with a polymer (rubber), particularly a vulcanizable polymer (rubber). The silica coupling agent acts as a connecting bridge between silica and the polymer. Suitable silica coupling agents include those containing groups such as alkyl alkoxy, mercapto, blocked mercapto, sulfide-containing (e.g., monosulfide-based alkoxy-containing, disulfide-based alkoxy-containing, tetrasulfide-based alkoxy-containing), amino, vinyl, epoxy, and combinations thereof. In certain embodiments, the silica coupling agent can be added to the rubber composition in the form of a pre-treated silica; a pre-treated silica has been pre-surface treated with a silane prior to being added to the rubber composition. The use of a pre-treated silica can allow for two ingredients (i.e., silica and a silica coupling agent) to be added in one ingredient, which generally tends to make rubber compounding easier.

Alkyl alkoxysilanes have the general formula R$^1_p$Si(OR$^2$)$_{4-p}$ where each R$^2$ is independently a monovalent organic group, and p is an integer from 1 to 3, with the proviso that at least one R$^1$ is an alkyl group. Preferably p is 1. Generally, each R$^1$ independently comprises C$_1$ to C$_{20}$ aliphatic, C$_5$ to C$_{20}$ cycloaliphatic, or C$_6$ to C$_{20}$ aromatic; and each R$^2$ independently comprises C$_1$ to C$_6$ aliphatic. In certain exemplary embodiments, each R$^1$ independently comprises C$_6$ to C$_{15}$ aliphatic and in additional embodiments each R$^1$ independently comprises C$_8$ to C$_{14}$ aliphatic. Mercapto silanes have the general formula HS—R$^3$—Si(R$^4$)(R$^5$)$_2$ where R$^3$ is a divalent organic group, R$^4$ is a halogen atom or an alkoxy group, each R$^5$ is independently a halogen, an alkoxy group or a monovalent organic group. The halogen is chlorine, bromine, fluorine, or iodine. The alkoxy group preferably has 1-3 carbon atoms. Blocked mercapto silanes have the general formula B—S—R$^6$—Si—X$_3$ with an available silyl group for reaction with silica in a silica-silane reaction and a blocking group B that replaces the mercapto hydrogen atom to block the reaction of the sulfur atom with the polymer. In the foregoing general formula, B is a block group which can be in the form of an unsaturated heteroatom or carbon bound directly to sulfur via a single bond; R$^6$ is C$_1$ to C$_6$ linear or branched alkylidene and each X is independently selected from the group consisting of C$_1$ to C$_4$ alkyl or C$_1$ to C$_4$ alkoxy.

Non-limiting examples of alkyl alkoxysilanes suitable for use in the rubber compositions of certain exemplary embodiments according to the first-third embodiments disclosed herein include, but are not limited to, octyltriethoxysilane, octyltrimethoxysilane, trimethylethoxysilane, cyclohexyltriethoxysilane, isobutyltriethoxy-silane, ethyltrimethoxysilane, cyclohexyl-tributoxysilane, dimethyldiethoxysilane, methyltriethoxysilane, propyltriethoxysilane, hexyltriethoxysilane, heptyltriethoxysilane, nonyltriethoxysilane, decyltriethoxysilane, dodecyltriethoxysilane, tetradecyltriethoxysilane, octadecyltriethoxysilane, methyloctyldiethoxysilane, dimethyldimethoxysilane, methyltrimethoxysilane, propyltrimethoxysilane, hexyltrimethoxysilane, heptyltrimethoxysilane, nonyltrimethoxysilane, decyltrimethoxysilane, dodecyltrimethoxysilane, tetradecyltrimethoxysilane, octadecyl-trimethoxysilane, methyloctyl dimethoxysilane, and mixtures thereof.

Non-limiting examples of bis(trialkoxysilylorgano) polysulfides suitable for use in the rubber compositions of certain exemplary embodiments according to the first-third embodiments disclosed herein include bis(trialkoxysilylorgano)disulfides and bis(trialkoxysilylorgano)tetrasulfides. Specific non-limiting examples of bis(trialkoxysilylorgano)disulfides suitable for use in the rubber compositions of certain exemplary embodiments according to the first-third embodiments disclosed herein include, but are not limited to, 3,3'-bis(triethoxysilylpropyl)disulfide, 3,3'-bis(trimethoxysilylpropyl)disulfide, 3,3'-bis(tributoxysilylpropyl)disulfide, 3,3'-bis(tri-t-butoxysilylpropyl)disulfide, 3,3'-bis(trihexoxysilylpropyl)disulfide, 2,2'-bis(dimethylmethoxysilylethyl)disulfide, 3,3'-bis(diphenylcyclohexoxysilylpropyl)disulfide, 3,3'-bis(ethyl-di-sec-butoxysilylpropyl)disulfide, 3,3'-bis(propyldiethoxysilylpropyl)disulfide, 12,12'-bis(triisopropoxysilylpropyl)disulfide, 3,3'-bis(dimethoxyphenylsilyl-2-methylpropyl)disulfide, and mixtures thereof. Non-limiting examples of bis(trialkoxysilylorgano)tetrasulfide silica coupling agents suitable for use in the rubber compositions of certain exemplary embodiments according to the first-third embodiments disclosed herein include, but are not limited to, bis(3-triethoxysilylpropyl) tetrasulfide, bis(2-triethoxysilylethyl)tetrasufide, bis(3-trimethoxysilylpropyl) tetrasulfide, 3-trimethoxysilylpropyl-N,N-dimethylthiocarbamoyl tetrasulfide, 3-triethoxysilylpropyl-N,N-dimethylthiocarbamoyl tetrasulfide, 2-triethoxysilyl-N,N-dimethylthiocarbamoyl tetrasulfide, 3-trimethoxysilylpropyl-benzothiazole tetrasulfide, 3-triethoxysilylpropylbenzothiazole tetrasulfide, and mixtures thereof. Bis(3-triethoxysilylpropyl) tetrasulfide is sold commercially as Si69® by Evonik Degussa Corporation.

Non-limiting examples of mercapto silanes suitable for use in the rubber compositions of certain exemplary embodiments of the first-third embodiments disclosed herein include, but are not limited to, 1-mercaptomethyltriethoxysilane, 2-mercaptoethyltriethoxysilane, 3-mercaptopropyltriethoxysilane, 3-mercaptopropylmethyldiethoxysilane, 2-mercaptoethyltripropoxysilane, 18-mercaptooctadecyldiethoxychlorosilane, and mixtures thereof.

Non-limiting examples of blocked mercapto silanes suitable for use in the rubber compositions of certain exemplary embodiments according to the first-third embodiments disclosed herein include, but are not limited to, those described in U.S. Pat. Nos. 6,127,468; 6,204,339; 6,528,673; 6,635,700; 6,649,684; and 6,683,135, the disclosures of which are hereby incorporated by reference. Representative examples of the blocked mercapto silanes for use herein in certain exemplary embodiments disclosed herein include, but are not limited to, 2-triethoxysilyl-1-ethylthioacetate; 2-trimethoxysilyl-1-ethylthioacetate; 2-(methyldimethoxysilyl)-1-ethylthioacetate; 3-trimethoxysilyl-1-propylthioacetate; triethoxysilylmethyl-thioacetate; triisopropoxysilylmethylthioacetate; trimethoxysilylmethylthioacetate; methyldimethoxysilylmethylthioacetate; methyldiethoxysilylmethylthioacetate; dimethylethoxysilylmethylthioacetate; methyldiisopropoxysilylmethylthioacetate; dimethylisopropoxysilylmethylthioacetate; 2-dimethylmethoxysilylmethylthioacetate; triisopropoxysilyl-1-ethylthioacetate; 2-(methyldiethoxysilyl)-1-ethylthioacetate, 2-(methyldiisopropoxysilyl)-1-ethylthioacetate; 2-(dimethylethoxysilyl-1-ethylthioacetate; 2-(dimethylmethoxysilyl)-1-ethylthioacetate; 2-(dimethylisopropoxysilyl)-1-ethylthioacetate; 3-triethoxysilyl-1-propylthioacetate; 3-triisopropoxysilyl-1-propylthioacetate; 3-methyldiethoxysilyl-1-propyl-thioacetate; 3-methyldimethoxysilyl-1-propylthioacetate; 3-methyldiisopropoxysilyl-1-propylthioacetate; 1-(2-triethoxysilyl-1-ethyl)-4-thioacetylcyclohexane; 1-(2-triethoxysilyl-1-ethyl)-3-thioacetylcyclohexane; 2-triethoxysilyl-5-thioacetylnorbornene; 2-triethoxysilyl-4-thioacetylnorbornene; 2-(2-triethoxysilyl-1-ethyl)-5-thioacetylnorbornene; 2-(2-triethoxy-silyl-1-ethyl)-4-thioacetylnorbornene; 1-(1-oxo-2-thia-5-triethoxysilylphenyl)benzoic acid; 6-triethoxysilyl-1-hexylthioacetate; 1-triethoxysilyl-5-hexylthioacetate; 8-triethoxysilyl-1-octylthioacetate; 1-triethoxysilyl-7-octylthioacetate; 6-triethoxysilyl-1-hexylthioacetate; 1-triethoxysilyl-5-octylthioacetate; 8-trimethoxysilyl-1-octylthioacetate; 1-trimethoxysilyl-7-octylthioacetate; 10-triethoxysilyl-1-decylthioacetate; 1-triethoxysilyl-9-decylthioacetate; 1-triethoxysilyl-2-butylthioacetate; 1-triethoxysilyl-3-butylthioacetate; 1-triethoxysilyl-3-methyl-2-butylthioacetate; 1-triethoxysilyl-3-methyl-3-butylthioacetate; 3-trimethoxysilyl-1-propylthiooctanoate; 3-triethoxysilyl-1-propyl-1-propylthiopalmitate; 3-triethoxysilyl-1-propylthiooctanoate; 3-triethoxysilyl-1-propylthiobenzoate; 3-triethoxysilyl-1-propylthio-2-ethylhexanoate; 3-methyldiacetoxysilyl-1-propylthioacetate; 3-triacetoxysilyl-1-propylthioacetate; 2-methyldiacetoxysilyl-1-ethylthioacetate; 2-triacetoxysilyl-1-ethylthioacetate; 1-methyldiacetoxysilyl-1-ethylthioacetate; 1-triacetoxysilyl-1-ethylthioacetate; tris-(3-triethoxysilyl-1-propyl)trithiophosphate; bis-(3-triethoxysilyl-1-propyl)methyldithiophosphonate; bis-(3-triethoxysilyl-1-propyl)ethyldithiophosphonate; 3-triethoxysilyl-1-propyldimethylthiophosphinate; 3-triethoxysilyl-1-propyldiethylthiophosphinate; tris-(3-triethoxysilyl-1-propyl)tetrathiophosphate; bis-(3-triethoxysilyl-1 propyl)methyltrithiophosphonate; bis-(3-triethoxysilyl-1-propyl)ethyltrithiophosphonate; 3-triethoxysilyl-1-propyldimethyldithiophosphinate; 3-triethoxysilyl-1-propyldicthyldithiophosphinate; tris-(3-methyldimethoxysilyl-1-propyl)trithiophosphate; bis-(3-methyldimethoxysilyl-1-propyl)methyldithiophosphonate; bis-(3-methyldimethoxysilyl-1-propyl)-ethyldithiophosphonate; 3-methyldimethoxysilyl-1-propyldimethylthiophosphinate; 3-methyldimethoxysilyl-1-propyldiethylthiophosphinate; 3-triethoxysilyl-1-propylmethylthiosulfate; 3-triethoxysilyl-1-propylmethanethiosulfonate; 3-triethoxysilyl-1-propylethanethiosulfonate; 3-triethoxysilyl-1-propylbenzenethiosulfonate; 3-triethoxysilyl-1-propyltoluenethiosulfonate; 3-triethoxysilyl-1-propylnaphthalenethiosulfonate; 3-triethoxysilyl-1-propylxylenethiosulfonate; triethoxysilylmethylmethylthiosulfate; triethoxysilylmethylmethanethiosulfonate; triethoxysilylmethylethanethiosulfonate; triethoxysilylmethylbenzenethiosulfonate; triethoxysilylmethyltoluenethiosulfonate; triethoxysilylmethylnaphthalenethiosulfonate; triethoxysilylmethylxylenethiosulfonate, and the like. Mixtures of various blocked mercapto silanes can be used. A further example of a suitable blocked mercapto silane for use in certain exemplary embodiments is NXT™ silane (3-octanoylthio-1-propyltriethoxysilane), commercially available from Momentive Performance Materials Inc. of Albany, NY.

Non-limiting examples of pre-treated silicas (i.e., silicas that have been pre-surface treated with a silane) suitable for use in the rubber compositions of certain exemplary embodiments according to the first-third embodiments disclosed herein include, but are not limited to, Ciptane® 255 LD and Ciptane® LP (PPG Industries) silicas that have been pre-treated with a mercaptosilane, and Coupsil® 8113 (Degussa) that is the product of the reaction between organosilane Bis(triethoxysilylpropyl) polysulfide (Si69) and Ultrasil® VN3 silica. Coupsil 6508, Agilon 400 ™ silica from PPG Industries, Agilon 454® silica from PPG Industries, and 458® silica from PPG Industries. In those embodiments of the rubber compositions and methods disclosed herein where the silica comprises a pre-treated silica, the pre-treated silica is used in an amount as previously disclosed for the reinforcing silica filler (i.e., about 5 to about 200 phr, including 5 to 200 phr, about 10 to about 200 phr, 10 to 200 phr, about 10 to about 175 phr, 10 to 175 phr, about 25 to about 150 phr, 25 to 150 phr, about 35 to about 150 phr, 35 to 150 phr, about 25 to about 125 phr, 25 to 125 phr, about 25 to about 100 phr, 25 to 100 phr, about 25 to about 80 phr, 25 to 80 phr, about 35 to about 125 phr, 35 to 125 phr, about 35 to about 100 phr, 35 to 100 phr, about 35 to about 80 phr, and 35 to 80 phr about 5 to about 200 phr, including about 25 to about 150 phr, about 35 to about 150 phr, about 25 to about 125 phr, about 25 to about 100 phr, about 25 to about 80 phr, about 35 to about 125 phr, about 35 to about 100 phr, and about 35 to about 80 phr).

When a silica coupling agent is utilized, the amount of silica coupling agent used in the rubber compositions according to the first-third embodiments disclosed herein may vary. In certain embodiments of the first-third embodiments disclosed herein, the rubber compositions do not contain any silica coupling agent. In other embodiments of the first-third embodiments disclosed herein, the silica coupling agent is present in an amount sufficient to provide a ratio of the total amount of silica coupling agent to reinforcing silica filler of about 1:100 to about 1:5 (i.e., about 0.01 to about 20 parts by weight per 100 parts of silica), including 1:100 to 1:5, about 1:100 to about 1:10, 1:100 to 1:10, about 1:100 to about 1:20, 1:100 to 1:20, about 1:100 to about 1:25, and 1:100 to 1:25 as well as about 1:100 to about 0:100 and 1:100 to 0:100. In certain embodiments according to the first-third embodiments disclosed herein, the rubber composition comprises about 0.01 to about 10 phr silica coupling agent, including 0.01 to 10 phr, about 0.01 to about 5 phr, 0.01 to 5 phr, about 0.01 to about 3 phr, and 0.01 to 3 phr.

Other Components of the Rubber Composition

In certain embodiments of the first-third embodiments, the rubber composition includes (i.e., further comprises) a cure package. Generally, the cure package includes at least one of: a vulcanizing agent; a vulcanizing accelerator; a vulcanizing activator (e.g., zinc oxide, stearic acid, and the like); a vulcanizing inhibitor, and an anti-scorching agent. In certain embodiments, the cure package includes at least one vulcanizing agent, at least one vulcanizing accelerator, at least one vulcanizing activator and optionally a vulcanizing inhibitor and/or an anti-scorching agent. Vulcanizing accelerators and vulcanizing activators act as catalysts for the vulcanization agent. Vulcanizing inhibitors and anti-scorching agents are known in the art and can be selected by one skilled in the art based on the vulcanizate properties desired.

Examples of suitable types of vulcanizing agents for use in the rubber compositions according to certain embodiments of the first-third embodiments, include but are not limited to, sulfur or peroxide-based curing components. Thus, in certain such embodiments, the curative component includes a sulfur-based curative or a peroxide-based curative. Examples of specific suitable sulfur vulcanizing agents include "rubbermaker's" soluble sulfur; sulfur donating curing agents, such as an amine disulfide, polymeric polysulfide, or sulfur olefin adducts; and insoluble polymeric sulfur. Preferably, the sulfur vulcanizing agent is soluble sulfur or a mixture of soluble and insoluble polymeric sulfur. For a general disclosure of suitable vulcanizing agents and other components used in curing, e.g., vulcanizing inhibitor and anti-scorching agents, one can refer to Kirk-Othmer, Encyclopedia of Chemical Technology, 3rd ed., Wiley Interscience, N. Y. 1982, Vol. 20, pp. 365 to 468, particularly Vulcanization Agents and Auxiliary Materials, pp. 390 to 402, or Vulcanization by A. Y. Coran, Encyclopedia of Polymer Science and Engineering, Second Edition (1989 John Wiley & Sons, Inc.), both of which are incorporated herein by reference. Vulcanizing agents can be used alone or in combination. Generally, the vulcanizing agents are used in an amount ranging from 0.1 to 10 phr, including from 1 to 7.5 phr, including from 1 to 5 phr, and preferably from 1 to 3.5 phr.

Vulcanizing accelerators are used to control the time and/or temperature required for vulcanization and to improve properties of the vulcanizate. Examples of suitable vulcanizing accelerators for use in the rubber compositions according to certain embodiments of the first-third embodiments disclosed herein include, but are not limited to, thiazole vulcanization accelerators, such as 2-mercaptobenzothiazole, 2,2'-dithiobis(benzothiazole) (MBTS), N-cyclohexyl-2-benzothiazole-sulfenamide (CBS), N-tert-butyl-2-benzothiazole-sulfonamide (TBBS), and the like; guanidine vulcanization accelerators, such as diphenyl guanidine (DPG) and the like; thiuram vulcanizing accelerators; carbamate vulcanizing accelerators; and the like. Generally, the amount of the vulcanization accelerator used ranges from 0.1 to 10 phr, preferably 0.5 to 5 phr.

Vulcanizing activators are additives used to support vulcanization. Generally vulcanizing activators include both an inorganic and organic component. Zinc oxide is the most widely used inorganic vulcanization activator. Various organic vulcanization activators are commonly used including stearic acid, palmitic acid, lauric acid, and zinc salts of each of the foregoing. Generally, the amount of vulcanization activator used ranges from 0.1 to 6 phr, preferably 0.5 to 4 phr.

Vulcanization inhibitors are used to control the vulcanization process and generally retard or inhibit vulcanization until the desired time and/or temperature is reached. Common vulcanization inhibitors include, but are not limited to, PVI (cyclohexylthiophthalmide) from Santogard. Generally, the amount of vulcanization inhibitor is 0.1 to 3 phr, preferably 0.5 to 2 phr.

Other ingredients that may be employed in the rubber compositions of certain embodiments of the first-third embodiments disclosed herein are well known to those of skill in the art and include oils (processing and extender), waxes, processing aids, anti-degradants such as antioxidants and anti-ozonants, tackifying resins, reinforcing resins, fatty acids, peptizers, zinc oxide, and the like. In certain embodiments of the first-third embodiments disclosed herein, the rubber composition comprises at least one of the following: a processing oil; an extender oil; a wax; a processing aid; an anti-degradant such as an antioxidant, an anti-ozonant, or both; a tackifying resin; a reinforcing resin; a fatty acid or a salt thereof; a peptizer; and zinc oxide; in certain such embodiments more than one of each type of ingredient may be utilized (e.g., more than one antioxidant, more than one processing aid, etc.).

Anti-degradants are ingredients added to protect the rubber from oxidative attack. ASTM D-4676 classifies rubber anti-degradants into six classes: p-phenylenediamines (PPDs), trimethyl-dihydroquinolines (TMQs), phenolics, alkylated diphenylamines (DPAs), aromatic phosphites, and diphenylamine-ketone condensates. In certain embodiments of the first-third embodiments disclosed herein, the rubber composition comprises at least one of the foregoing anti-degradants.

As discussed above, in certain embodiments of the first-third embodiments disclosed herein, the bio-oil from a recombinant cell may be utilized in combination with at least one additional oil (processing, extender or both). When at least one additional oil is utilized (i.e., in addition to the bio-oil from a recombinant cell) it may be a petroleum oil or a plant-sourced oil. In certain embodiments of the first-third embodiments disclosed herein, the rubber composition further comprises at least one petroleum oil, at least one plant-sourced oil (in addition to the bio-oil from a recombinant cell), or both. In certain embodiments of the first-third embodiments disclosed herein, the rubber composition is essentially free of any plant oil other than the bio-oil from a recombinant cell. In certain embodiments of the first-third embodiments disclosed herein, the rubber composition is essentially free of any petroleum oil. Essentially free of can be understood as a rubber composition containing no more than 5 phr, including no more than 1 phr, and 0 phr. Various types of petroleum oils are well known and may be suitable for use as an additional oil (processing, extender, or both) in the rubber compositions of certain embodiments of the first-third embodiment disclosed herein, including, but not limited to aromatic, naphthenic, and low PCA oils. Suitable low PCA oils include those having a polycyclic aromatic content of less than 3 percent by weight as determined by the IP346 method. Procedures for the IP346 method may be found in Standard Methods for Analysis & Testing of Petroleum and Related Products and British Standard 2000 Parts, 2003, 62nd edition, published by the Institute of Petroleum, United Kingdom. Suitable low PCA oils include mild extraction solvates (MES), treated distillate aromatic extracts (TDAE), TRAE, and heavy naphthenics. Suitable MES oils are available commercially as CATENEX SNR from SHELL, PROREX 15, and FLEXON 683 from EXXONMOBIL, VIVATEC 200 from BP, PLAXOLENE MS from TOTAL FINA ELF, TUDALEN 4160/4225 from DAHLEKE, MES-H from REPSOL, MES from Z8, and OLIO MES S201 from AGIP. Suitable TDAE oils are available as TYREX 20 from EXXONMOBIL, VIVATEC 500, VIVATEC 180, and ENERTHENE 1849 from BP, and EXTENSOIL 1996 from REPSOL. Suitable heavy naphthenic oils are available as SHELLFLEX 794, ERGON BLACK OIL, ERGON H2000, CROSS C2000, CROSS C2400, and SAN JOAQUIN 2000L. Preferably, the rubber composition of the first-third embodiments is essentially free any petroleum oil. Suitable low PCA oils also include various plant-sourced oils such as can be harvested from vegetables, nuts, and seeds. Non-limiting examples include, but are not limited to, soy or soybean oil, sunflower oil, safflower oil, corn oil, linseed oil, cotton seed oil, rapeseed oil, cashew oil, sesame oil, camellia oil, jojoba oil, macadamia nut oil, coconut oil, and palm oil. The foregoing processing oils can also be used as an extender oil, i.e., to prepare an oil-extended polymer or copolymer. Generally, for most tire and tire component applications the total amount of oil used (processing oil and extender oil) in the rubber compositions and methods disclosed herein ranges from about 5 to about 70 phr, including 5 to 70 phr, about 5 to about 60 phr, about 5 to about 60 phr, about 5 to about 50 phr, and 5 to 50 phr; the total amount of oil should be understood to include both the bio-oil from a recombinant cell and any additional oil. However, in certain tire and tire component applications, the total amount of oil used (processing oil and extender oil) in the rubber compositions and methods disclosed herein is much higher and ranges up to about 175 phr, including up to 175 phr, up to about 150 phr, up to 150 phr, up to about 100 phr, and up to 100 phr.

Methods for Preparing Rubber Compositions

The rubber compositions according to the first-third embodiments disclosed herein may generally be formed by mixing together the ingredients for the rubber composition (as disclosed above) by methods known in the art, such as, for example, by kneading the ingredients together in a Banbury mixer or on a milled roll. The methods generally include at least one non-productive master-batch mixing stage and a final productive mixing stage. The term non-productive master-batch stage is known to those of skill in the art and generally understood to be a mixing stage where no vulcanizing agents or vulcanization accelerators are added. The term final productive mixing stage is also known to those of skill in the art and generally understood to be the mixing stage where the vulcanizing agents and vulcanization accelerators are added into the rubber composition. In certain embodiments of the compositions and methods disclosed herein, more than one non-productive master-batch mixing stage may be used. In certain embodiments of the compositions and methods disclosed herein, more than one non-productive master-batch mixing stage is used and the bio-oil from a recombinant cell is added in the first (initial) master-batch stage. In other embodiments of the compositions and methods disclosed herein, at least two non-productive master-batch mixing stages are used and the bio-oil from a recombinant cell is added in the second master-batch stage. In other embodiments of the compositions and methods disclosed herein, at least two non-productive master-batch mixing stages are used and the bio-oil from a recombinant cell is added in more than one master-batch stage. In yet other embodiments of the compositions and methods disclosed herein, more than one non-productive master-batch mixing stage is used and the bio-oil from a recombinant cell is added in the last non-productive master-batch mixing stage.

In certain embodiments of the methods for preparing rubber compositions according to the first-third embodiments disclosed herein, the non-productive master batch mixing stage(s) may be conducted at a temperature of about 130° C. to about 200° C. In certain embodiments, the final productive mixing stage may be conducted at a temperature below the vulcanization temperature in order to avoid unwanted pre-cure of the rubber composition. Therefore, the temperature of the productive mixing stage should not exceed about 120° C. and is typically about 40° C. to about 120° C., or about 60° C. to about 110° C. and, especially, about 75° C. to about 100° C.

In certain embodiments of the first-third embodiments disclosed herein, a rubber composition is prepared according to a method that includes at least one non-productive mixing stage and at least one productive mixture stage. In certain embodiments, the method for preparing the rubber compositions of the present disclosure includes: (1) mixing, in at least one non-productive master-batch stage, a rubber composition comprising: 100 phr of at least one rubber; from about 5 to about 200 phr (including 5 to 200 phr) of at least one reinforcing filler; and about 5 to about 50 phr of bio-oil from a recombinant cell; and (2) mixing the resulting product of the non-productive master batch in a final productive stage along with at least one curative, such as a curative package, as discussed above. With respect to certain embodiments of the first embodiment disclosed herein, the list of ingredients should be understood as including ingredients to be mixed to form the rubber composition. With respect to the certain embodiments of the second embodiment disclosed herein (i.e., a rubber composition that has been subjected to curing), the list of ingredients should be understood to comprise the ingredients present in the cured rubber composition.

Tires and Tire Components

As previously discussed, certain embodiments disclosed herein include tires, tire treads, and tire sidewalls comprising a rubber composition of the second embodiments as otherwise disclosed herein, i.e., comprising at least one rubber and about 5 to about 50 phr of bio-oil from a recombinant cell. More specifically, the present disclosure includes a tire comprising a rubber composition of the first-third embodiments as otherwise disclosed herein, a tire comprising a tire tread comprising a rubber composition of the first-third embodiments as otherwise disclosed herein, a tire tread comprising a rubber composition of the first-third embodiments as otherwise disclosed herein, a tire comprising a tire sidewall comprising a rubber composition of the first-third embodiments as otherwise disclosed herein, and a tire sidewall comprising a rubber composition of the first-third embodiments as otherwise disclosed herein. Generally, when the rubber compositions of the first-third embodiments disclosed herein are utilized in tires, tire treads, or tire sidewalls, these compositions are processed into tire components according to ordinary tire manufacturing techniques including standard rubber shaping, molding, and curing techniques. Any of the various rubber tire components can be fabricated including, but not limited to, treads, sidewalls, belt skims, and carcass. Typically, vulcanization of a tire component is effected by heating the vulcanizable composition in a mold; e.g., it may be heated to about 140° C. to about 180° C. Cured or crosslinked rubber compositions may be referred to as vulcanizates, which generally contain three-dimensional polymeric networks that are thermoset. The other ingredients, such as processing aides and fillers, may be evenly dispersed throughout the vulcanized network. In certain embodiments, pneumatic tires containing the rubber compositions as disclosed herein can be produced as discussed in U.S. Pat. Nos. 5,866,171, 5,876,527, 5,931,211, and 5,971,046, which are incorporated herein by reference.

Methods of Controlling the Variability of Fatty Acid Content

As discussed above, in a first embodiment, a method is disclosed for controlling the variability of fatty acid content in a bio-oil-containing rubber composition. The method comprises incorporating about 5 to about 100 phr of bio-oil produced by a recombinant cell with at least one rubber, at least one reinforcing filler, and a cure package, thereby forming a bio-oil-containing rubber composition. By the method of the first embodiment, a bio-oil produced by a recombinant cell is used in a rubber composition instead of (or in certain embodiments in addition to) a bio-oil obtained from a plant. The use of bio-oil produced by a recombinant cell such as an algal cell controls (or reduces) the variability in fatty acid content that would otherwise occur when a plant-sourced bio-oil is utilized. Plant-sourced bio-oils can vary widely in fatty acid content depending upon various conditions such as time of planting, weather conditions, and location of the crop. For example, according to Robertson, et al., "Effect of Planting Date on Sunflower Seed Content, Fatty Acid Composition and Yield in Florida," Journal of the American Oil Chemists' Society, June 1981, Volume 58, Issue 6, pp 698-701, time of planting at the same location caused the mean oleic acid content in sunflower seeds to vary from 54.6% (April 2 planting) to 19.4% (August 14 planting) and the linoleic acid content to vary from 36.3% (April 2 planting) to 68.4% (August 14 planting). Similarly, Unger reported on the variation in oleic acid and linoleic acid content in sunflowers grown in northern Texas, finding a variation in oleic acid content of from 16.3% (July 28-August 1 planting) to 44.8% (April 17-26 planting) and a variation in linoleic acid content of from 71.6% (July 15-19 planting) to 43.3% (April 17-26 planting). "Planting Date Effects On Growth, Yield, And Oil of Irrigated Sunflower," Agronomy Journal, vol. 72, November-December 1980, pp. 914-16. Thus, plant-sourced bio-oils can vary in fatty acid content by more than 100%, sometimes more than 200%, and in certain instances as much as almost 300%. Such variations can make quality control or meeting an internal specification for a plant-sourced bio-oil difficult to maintain within acceptable limits. The use of a bio-oil produced by a recombinant cell such as an algal cell can alleviate this difficulty by providing a bio-oil with little, if any, variation in fatty acid content. In certain embodiments, the bio-oil produced by a recombinant cell has a variation in the content of a particular fatty acid of less than +/−5%, preferably less than +/−3%, and more preferably less than +/−1% (the percentages being determined based upon the particular amount of fatty acid so that a content that averages 20% oleic acid but ranges from 16% to 24% would be considered to have a variation of +/−20%).

Methods of Providing a Bio-Oil Containing Tire with a Reduced Carbon Footprint

In a second embodiment, a method is disclosed for providing a bio-oil-containing tire with a reduced carbon footprint. The method comprises incorporating about 5 to about 100 phr of bio-oil produced by a recombinant cell into at least one rubber, at least one reinforcing filler, and a cure package, thereby forming an oil-containing rubber composition, and incorporating the oil-containing rubber composition into at least one component of a tire, thereby producing a reduced carbon footprint oil containing tire. By the method of the second embodiment, a bio-oil produced by a recombinant cell is used in a rubber composition instead of a bio-oil obtained from a plant. A significant amount of fossil fuel products (e.g., gasoline, oil, and products such as fertilizers made therefrom) are expended growing and harvest plants to produce bio-oils. The use of bio-oils produced by recombinant cells such as algal cells offers a source of bio-oil that is produced using a lesser amount of fossil fuel products. Accordingly, the incorporation of bio-oil produced by a recombinant cell into a rubber composition and the incorporating of the oil-containing rubber composition into at least one component of a tire, will result in a tire having a reduced carbon footprint. The phrase reduced carbon footprint should be understood to include not only the amount of petroleum-based products used in the tire, but also the amount of fossil fuel products used to produce the bio-oil(s) contained within the tire.

EXAMPLES

The following examples illustrate specific and exemplary embodiments and/or features of the embodiments of the present disclosure. The examples are provided solely for the purposes of illustration and should not be construed as limitations of the present disclosure. Numerous variations over these specific examples are possible without departing from the spirit and scope of the presently disclosed embodiments. More specifically, the particular rubbers, fillers, and other ingredients (e.g., antioxidant, and curative package ingredients) utilized in the following examples should not be interpreted as limiting since other such ingredients consistent with the disclosure in the Detailed Description can be utilized in substitution. In other words, the particular rubbers, fillers, and other ingredients as well as their amounts and their relative amounts in the following examples should be understood to apply to the more general content of the detailed description.

Examples 1 to 8

In Examples 1 to 8, rubber compositions were prepared comprising rubber (natural rubber in combination with one of: solution SBR, high-cis polybutadiene, low-cis polybutadiene, or functionalized SBR), carbon black filler, and either a petroleum oil or a bio-oil produced by a recombinant (algal) cell. The functionalized SBR was functionalized with tin, producing a carbon-black reactive polymer. The bio-oil produced by a recombinant (algal) cell was obtained from Solazyme, Inc. (San Francisco, California), under their designation S3168; the oil is referred to within the Tables as "Algal oil." The rubber compositions of Examples 1 to 8 were prepared in a four stage mixing process (i.e., one master-batch stage, and a final batch stage) according to the formulations shown in Table 1A. The amount of each ingredient used is reported as parts per hundred rubber (phr). The mixing processes used for these formulations are outlined in Table 1B. The indexed data reported in Table 1C has been prepared relative to the data for the respective control composition (e.g., Example 1 is the control for Example 2, Example 3 is the control for Example 4, Example 5 is the control for Example 6, and Example 7 is the control for Example 8), and calculated so that an improvement (i.e., a movement in a property towards a more desirable measurement) appears as a number greater than 1 and a property that moves towards a less desirable measurement appears as a number less than 1. Such an indexing system was used to account for the fact that for some properties an increase in the measured value is desirable whereas for other properties a decrease in the measured value is desirable. Properties deemed to show an improvement when the value increased are indicated using the symbol ^ in Table 1C.

TABLE 1A

Formulation matrix for algal oil with four polymeric systems with carbon black

| Stocks# | 1 sSBR w/proc. oil | 2 SSBR w/algal oil | 3 high-cis BR w/proc. oil | 4 high-cis BR w/algal oil | 5 low-cis BR w/proc. oil | 6 low-cis BR w/algal oil | 7 CB-func. Poly. w/proc. oil | 8 CB-func. Poly. w/algal oil |
|---|---|---|---|---|---|---|---|---|
| Master-Batch #1 | | | | | | | | |
| s-SBR[1] | 80 | 80 | 0 | 0 | 0 | 0 | 0 | 0 |
| High-cis Polybutadiene[2] | 0 | 0 | 80 | 80 | 0 | 0 | 0 | 0 |
| Low-cis Polybutadiene[3] | 0 | 0 | 0 | 0 | 80 | 80 | 0 | 0 |
| Functionalized Polymer[4] | 0 | 0 | 0 | 0 | 0 | 0 | 80 | 80 |
| Natural Rubber | 20 | 20 | 20 | 20 | 20 | 20 | 20 | 20 |

TABLE 1A-continued

Formulation matrix for algal oil with four polymeric systems with carbon black

| Stocks# | 1 sSBR w/proc. oil | 2 SSBR w/algal oil | 3 high-cis BR w/proc. oil | 4 high-cis BR w/algal oil | 5 low-cis BR w/proc. oil | 6 low-cis BR w/algal oil | 7 CB-func. Poly. w/proc. oil | 8 CB-func. Poly. w/algal oil |
|---|---|---|---|---|---|---|---|---|
| Carbon black | 50 | 50 | 50 | 50 | 50 | 50 | 50 | 50 |
| Processing oil[5] | 10 | | 10 | | 10 | | 10 | |
| Bio-oil from Recombinant cell[6] | 0 | 10 | 0 | 10 | 0 | 10 | 0 | 10 |
| Curative #1 | 2 | 2 | 2 | 2 | 2 | 2 | 2 | 2 |
| Antioxidant/ Anti degradant | 2.95 | 2.95 | 2.95 | 2.95 | 2.95 | 2.95 | 2.95 | 2.95 |
| Final Batch | | | | | | | | |
| Curative #2 | 2.5 | 2.5 | 2.5 | 2.5 | 2.5 | 2.5 | 2.5 | 2.5 |
| Vulcanizing agent | 1.5 | 1.5 | 1.5 | 1.5 | 1.5 | 1.5 | 1.5 | 1.5 |
| Vulcanization accelerators | 1.3 | 1.3 | 1.3 | 1.3 | 1.3 | 1.3 | 1.3 | 1.3 |

[1]Styrene-butadiene copolymer prepared by solution polymerization and containing 23.5% styrene.
[2]High-cis polybutadiene (96% cis)'
[3]Low-cis polybutadiene (33% cis).
[4]Styrene butadiene copolymer or polybutadiene, tin functionalized.
[5]Low PCA oil, Black Oil from Ergon Manufacturing.
[6]This oil contained 80% oleic acid, 8% linoleic acid, 0.3% alpha-linolenic, with 9% saturated fatty acids having C10-C24 and less than 0.1% free fatty acids.

TABLE 1B

Mixing Parameters for carbon black-containing compositions

| Stage | Time | Condition |
|---|---|---|
| Master-Batch Stage 1 (initial temp: 160° C., rotor rpm started at 115) | 0 seconds 15 seconds | Charge polymers Charge any oil, filler (e.g., any carbon black) and other master-batch ingredients Drop ram after 120 seconds |
| Final Batch Stage (initial temp: 98° C., rotor rpm at 40) | 0 seconds 0 seconds | Charge curatives, AO, accelerators Drop based on max temperature of 210° F. (99° C.) |

Each of the rubber compositions was subjected to testing to measure various properties. Results are reported below in Table 1C. Samples were tested by tensile testing to measure the elastic properties of the composition. The abbreviation $E_b$ is used for elongation at break and $T_b$ for stress at break, which measurements provides an indication of a rubber component's tear resistance, which is particularly relevant when it is incorporated into a tire tread. The abbreviation M300 is used for the tensile stress measured at 300% elongation.

Tensile mechanical properties of the samples were determined following the guidelines, but not restricted to, the standard procedure described in ASTM D-412, using dumbbell-shaped samples with a cross-section dimension of 4 mm in width and 1.9 mm in thickness at the center. Specimens were strained at a constant rate and the resulting force was recorded as a function of extension (strain). The specimens were tested at 23° C. The elongation at break was measured after 40 minutes and after sweeping the temperature from either 25° C. or 100° C. to 150° C. Samples were cured for 40 minutes at 150° C., and then tensile properties were analyzed at 25° C. and at 100° C.

Tan δ values were measured using a dynamic compression test done with a Dynastat™ mechanical spectrometer (Dynastatics Instruments Corp.; Albany, New York) using a cylindrical button geometry test specimen (7.8 mm diameter×6 mm height). The temperature was held constant at the desired temperature: 0° C., 30° C., or 60° C. The sample was compressed under a static load of 2 kg before testing. After it reached an equilibrium state, the test started with a dynamic compression load of 1.25 kg at a frequency of 15 Hz. The sample was then dynamically compressed and then extended and the resultant hysteresis (tan δ) was then recorded. A rubber composition's tan δ at 0° C. is indicative of its wet traction when incorporated into a tire tread, its tan δ at 30° C. is indicative of its dry traction when incorporated into a tire tread and its tan δ at 60° C. is indicative of its rolling resistance when incorporated into a tire tread.

The viscosities disclosed herein are real dynamic viscosities determined using an Alpha Technologies RPA (Rubber Process Analyzer) instrument which is rotorless. Measurements were made following the guidance of, but not strictly according to ASTM D 6204. In accordance with ASTM D 6204, a three point frequency sweep was conducted. The rubber compositions were pre-heated for 1 minute at 130° C. In accordance with the ASTM procedure, strain sweep was conducted at 130 C, strain at 100 percent, and 1 Hz were conducted. The viscosity data reported is from a run conducted at 266° F., G' at 2 minutes.

TABLE 1C

| Property | 1 sSBR w/proc. oil | 2 sSBR w/algal oil | 3 high cis BR w/proc. oil | 4 high cis BR w/algal oil | 5 low cis BR w/proc. oil | 6 low cis BR w/algal oil | 7 funct. Poly w/proc. oil | 8 funct. Poly w/algal oil |
|---|---|---|---|---|---|---|---|---|
| Indexed M300^ | 1.00 | 0.95 | 1.00 | 0.89 | 1.00 | 0.91 | 1.00 | 0.90 |
| Indexed Tb^ | 1.00 | 0.88 | 1.00 | 0.91 | 1.00 | 0.86 | 1.00 | 0.70 |
| Indexed Eb^ | 1.00 | 1.01 | 1.00 | 1.02 | 1.00 | 0.95 | 1.00 | 0.85 |
| Indexed tan δ 0° C.^ | 1.00 | 0.95 | 1.00 | 0.97 | 1.00 | 0.97 | 1.00 | 0.96 |
| Indexed tan δ 30° C.^ | 1.00 | 0.97 | 1.00 | 0.96 | 1.00 | 0.98 | 1.00 | 0.99 |
| Indexed E'^ | 1.00 | 0.89 | 1.00 | 0.80 | 1.00 | 0.875 | 1.00 | 0.95 |
| Indexed tan δ 60° C. | 1.00 | 1.02 | 1.00 | 1.04 | 1.00 | 1.02 | 1.00 | 0.99 |
| Indexed viscosity | 1.00 | 1.03 | 1.00 | 1.02 | 1.00 | 0.99 | 1.00 | 0.99 |
| Indexed wear | 100 | 111 | 100 | 127 | 100 | 111 | 100 | 116 |

As can be seen from the data in Table 1C, the addition of bio-oil produced by a recombinant (algal) cell to any of the four rubber compositions results in an improvement in the wear rate (i.e., reduced wear) for all four rubber types; an improvement to comparable Tb in the composition containing high-cis BR; an improvement to comparable Eb in the compositions comprising SBR, high-cis BR, or low-cis BR; an improvement to comparable tan δ at 0° C. for all four rubber types; an improvement to comparable tan δ at 30° C. for all four rubber types; an improvement to comparable E' for the composition comprising functionalized polymer; an improvement to comparable tan δ at 60° C. for all four rubber types; and an improvement to comparable effect on viscosity for all four rubber types. (Comparable being used as including an index value of no less than 0.9.)

Examples 9 to 16

In Examples 9 to 16, rubber compositions were prepared comprising rubber (natural rubber in combination with one of: solution SBR (s-SBR), high-cis polybutadiene, low-cis polybutadiene, or functionalized SBR), silica filler, and either a petroleum-based processing oil or a bio-oil produced by a recombinant (algal) cell. The functionalized SBR contained silica-reactive functionality, producing a silica-reactive polymer. The bio-oil produced by a recombinant (algal) cell was obtained from Solazyme, Inc. (San Francisco, California), under their designation S3168; the oil is referred to within the Tables as "Algal oil." The rubber compositions of Examples 9 to 16 were prepared in a four stage mixing process (i.e., two master-batch stages, a remill, and a final batch stage) according to the formulations shown in Table 2A. The amount of each ingredient used is reported as parts per hundred rubber (phr). The mixing processes used for these formulations are outlined in Table 2B. The indexed data reported in Table 2C was prepared in the same manner described above for Example 1 to 8.

TABLE 2A

Formulation matrix for algal oil with four polymeric systems with silica

| Stocks# | 1 sSBR w/proc. oil | 2 sSBR w/algal oil | 3 high-cis BR w/proc. oil | 4 high-cis BR w/algal oil | 5 low-cis BR w/proc. oil | 6 low-cis BR w/algal oil | 7 silica-func. Poly. w/proc. oil | 8 silica func. Poly. w/algal oil |
|---|---|---|---|---|---|---|---|---|
| Master-Batch #1 | | | | | | | | |
| S-SBR[1] | 80 | 80 | 0 | 0 | 0 | 0 | 0 | 0 |
| High-cis Polybutadiene[2] | 0 | 0 | 80 | 80 | 0 | 0 | 00 | |
| Low-cis Polybutadiene[3] | 0 | 0 | 0 | 0 | 80 | 80 | 0 | 0 |
| Functionalized Polymer[4] | 0 | 0 | 0 | 0 | 0 | 0 | 80 | 80 |
| Natural rubber | 20 | 20 | 20 | 20 | 20 | 20 | 20 | 20 |
| Silica filler | 52.5 | 52.5 | 52.5 | 52.5 | 52.5 | 52.5 | 52.5 | 52.5 |
| Processing oil[5] | 10 | 0 | 10 | 0 | 10 | 0 | 10 | 0 |
| Algal oil[6] | 0 | 10 | 0 | 10 | 0 | 10 | 0 | 10 |
| Curative #1 | 0 | 0.6 | 1.2 | 0 | 0.6 | 1.2 | 0.6 | 1.2 |
| Antioxidant/ Antidegradant | 4 | 4 | 4 | 4 | 4 | 4 | 4 | 4 |
| Master-Batch #2 | | | | | | | | |
| Silica | 2.5 | 2.5 | 2.5 | 2.5 | 2.5 | 2.5 | 2.5 | |
| Silica coupling agent (silane) | 5 | 5 | 5 | 5 | 5 | 5 | 5 | 5 |

TABLE 2A-continued

Formulation matrix for algal oil with four polymeric systems with silica

| Stocks# | 1 sSBR w/proc. oil | 2 sSBR w/algal oil | 3 high-cis BR w/proc. oil | 4 high-cis BR w/algal oil | 5 low-cis BR w/proc. oil | 6 low-cis BR w/algal oil | 7 silica-func. Poly. w/proc. oil | 8 silica func. Poly. w/algal oil |
|---|---|---|---|---|---|---|---|---|
| Final Batch | | | | | | | | |
| Curative #2 | 2.5 | 2.5 | 2.5 | 2.5 | 2.5 | 2.5 | 2.5 | 2.5 |
| Vulcanizing agent | 1.5 | 1.5 | 1.5 | 1.5 | 1.5 | 1.5 | 1.5 | 1.5 |
| Vulcanization accelerators | 4.1 | 4.1 | 4.1 | 4.1 | 4.1 | 4.1 | 4.1 | 4.1 |

[1] Styrene-butadiene copolymer prepared by solution polymerization and containing 23.5% styrene.
[2] High-cis polybutadiene (96% cis)'
[3] Low-cis polybutadiene (33% cis).
[4] Styrene-butadiene copolymer with silica reactive functionality.
[5] Low PCA oil, Black Oil from Ergon Manufacturing.
[6] This oil contained 80% oleic acid, 8% linoleic acid, 0.3% alpha-linolenic, with 9% saturated fatty acids having C10-C24 and less than 0.1% free fatty acids.

TABLE 2B

Mixing Parameters for silica-containing compositions

| Stage | Time | Condition |
|---|---|---|
| Master-Batch Stage 1 (initial temp: 105° C., rotor rpm started at 60) | 0 seconds 30 seconds | Charge polymers Charge any oil, filler (e.g., any carbon blac kand/or silica) and other master-batch ingredients, increase rotor to 75 rpm Drop based on max temperature of 310° F. (154° C.) |
| Master-Batch Stage 2 (initial temp: 105° C., rotor rpm started at 60) | 0 seconds | Charge additional ingredients listed under Master-Batch #2 Drop based on max temperature of 300° F. (149° C.) |
| Remill Stage (initial temp: 105° C., rotor rpm at 60) | 0 seconds | Charge Master Batch from #2 Drop based on max temperature of 300° F. (149° C.) |
| Final Batch Stage (initial temp: 80° C., rotor rpm at 40) | 0 seconds 0 seconds | Charge Remill Charge curatives Drop based on max temperature of 210° F. (99° C.) |

As can be seen from the data in Table 2C, the addition of bio-oil produced by a recombinant (algal) cell to any of the four rubber compositions results in an improvement in the wear rate (i.e., reduced wear) for all four rubber types, an improvement to comparable Tb in the compositions containing SBR, high-cis BR or functionalized polymer; an improvement to comparable Eb in the compositions comprising SBR, high-cis BR, or functionalized polymer; an improvement to comparable tan δ at 0° C. in the compositions comprising SBR or low-cis BR; an improvement to comparable tan δ at 30° C. for all four rubber types; an improvement to comparable E' for all four rubber types; an improvement to comparable tan δ at 60° C. for all four rubber types; and an improvement in viscosity for all four rubber types. (Comparable being used as including an index value of no less than 0.9.)

This application discloses several numerical range limitations that support any range within the disclosed numerical ranges, even though a precise range limitation is not stated verbatim in the specification, because the embodiments of the compositions and methods disclosed herein could be practiced throughout the disclosed numerical ranges. With respect to the use of substantially any plural or singular terms herein, those having skill in the art can translate from

TABLE 2C

| Property | 1 sSBR w/proc. oil | 2 sSBR w/algal oil | 3 high cis BR w/proc. oil | 4 high cis BR w/algal oil | 5 low cis BR w/proc. oil | 6 low cis BR w/algal oil | 7 funct. Poly w/proc. oil | 8 funct. Poly w/algal oil |
|---|---|---|---|---|---|---|---|---|
| Indexed M300^ | 1.00 | 0.92 | 1.00 | 0.92 | 1.00 | 1.02 | 1.00 | 0.85 |
| Indexed Tb^ | 1.00 | 0.96 | 1.00 | 1.00 | 1.00 | 0.82 | 1.00 | 1.09 |
| Indexed Eb^ | 1.00 | 1.02 | 1.00 | 1.10 | 1.00 | 0.73 | 1.00 | 1.21 |
| Indexed tan δ 0° C.^ | 1.00 | 0.91 | 1.00 | 0.79 | 1.00 | 1.05 | 1.00 | 0.84 |
| Indexed tan δ 30° C.^ | 1.00 | 1.00 | 1.00 | 0.99 | 1.00 | 1.02 | 1.00 | 0.92 |
| Indexed E'^ | 1.00 | 0.95 | 1.00 | 0.99 | 1.00 | 1.19 | 1.00 | 1.11 |
| Indexed tan δ 60° C. | 1.00 | 0.99 | 1.00 | 1.02 | 1.00 | 1.04 | 1.00 | 0.97 |
| Indexed viscosity | 1.00 | 1.01 | 1.00 | 1.06 | 1.00 | 1.05 | 1.00 | 1.02 |
| Indexed wear | 100 | 108 | 100 | 152 | 100 | 120 | 100 | 120 | the plural to the singular or from the singular to the plural as is appropriate to the context or application. The various singular or plural permutations may be expressly set forth herein for sake of clarity.

It will be understood by those within the art that, in general, terms used herein, and especially in the appended claims are generally intended as "open" terms. For example, the term "including" should be interpreted as "including but not limited to," the term "having" should be interpreted as "having at least," the term "includes" should be interpreted as "includes but is not limited to." It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references, including but not limited to patents, patent applications, and non-patent literature are hereby incorporated by reference herein in their entirety.

While various aspects and embodiments of the compositions and methods have been disclosed herein, other aspects and embodiments will be apparent to those skilled in the art. The various aspects and embodiments disclosed herein are for purposes of illustration and are not intended to be limiting, with the true scope and spirit being indicated by the claims.

What is claimed is:

1. A bio-oil-containing rubber composition, comprising
   1 to 100 phr of bio-oil produced by a recombinant cell,
   at least one rubber including at least one diene monomer-containing polymer or copolymer,
   5 to 150 phr of at least one reinforcing filler, and
   a cure package, wherein the at least one reinforcing filler comprises at least one of carbon black and silica and the amount of carbon black is no more than 30% by weight of the total amount of reinforcing filler, and wherein the at least one rubber includes 10 to 90 phr of functionalized polybutadiene having a cis 1,4-bond content of at least 90%, and wherein the at least one rubber does not include an oil-extended rubber.

2. The rubber composition of claim 1, wherein the recombinant cell comprises an algal cell.

3. The rubber composition of claim 1, wherein the bio-oil is present in an amount of 5 to 50 phr.

4. The rubber composition of claim 1, wherein the bio-oil has a linoleic acid content of about 45% to about 65% by weight, an oleic acid content of about 20% to about 30% by weight, and a palmitic acid content of about 5% to about 15% by weight.

5. The rubber composition of claim 1, wherein the functionalized polybutadiene is functionalized with a silicon containing functional group selected from the group consisting of an alkoxysilyl group, an alkylhalosilyl group, a siloxy group, an alkylaminosilyl group, and an alkoxyhalosilyl group.

6. The rubber composition of claim 1, wherein the bio-oil has an oleic acid content of at least about 70% and a linoleic acid content of at least about 5%.

7. The rubber composition of claim 1, wherein the bio-oil produced by a recombinant cell has either:
   at least 50% of its carbon content as naphthenic carbons, or
   at least 50% of its carbon content as paraffinic carbons.

8. A tire component comprising the rubber composition of claim 1.

9. A tire tread comprising the rubber composition of claim 1.

10. A method for improving at least one of the wear rate or E' of a rubber composition, the method comprising
    incorporating about 1 to about 100 phr of bio-oil produced by a recombinant cell into
    at least one rubber including at least one diene monomer-containing polymer or copolymer,
    5 to 200 phr of at least one reinforcing filler, and
    a cure package,
    wherein the at least one reinforcing filler comprises at least one of carbon black and silica and the amount of carbon black is no more than 30% by weight of the total amount of reinforcing filler, and wherein the at least one rubber includes 10 to 90 phr of functionalized polybutadiene having a cis 1,4-bond content of at least 90%, wherein the at least one rubber does not include an oil-extended rubber.

11. The rubber method of claim 10, wherein the recombinant cell comprises an algal cell.

12. The method of claim 10, wherein the bio-oil is present in an amount of 5 to 50 phr.

13. The method of claim 10, wherein the bio-oil has a linoleic acid content of about 45% to about 65% by weight, an oleic acid content of about 20% to about 30% by weight, and a palmitic acid content of about 5% to about 15% by weight.

14. The method of claim 10, wherein the functionalized polybutadiene is functionalized with a silicon containing functional group selected from the group consisting of an alkoxysilyl group, an alkylhalosilyl group, a siloxy group, an alkylaminosilyl group, and an alkoxyhalosilyl group.

15. The method of claim 10, wherein the bio-oil has an oleic acid content of at least about 70% and a linoleic acid content of at least about 5%.

16. The method of claim 10, wherein the bio-oil produced by a recombinant cell has either:
    at least 50% of its carbon content as naphthenic carbons, or
    at least 50% of its carbon content as paraffinic carbons.

17. A method for controlling the variability of fatty acid content in a bio-oil-containing rubber composition, comprising incorporating about 1 to about 100 phr of bio-oil produced by a recombinant cell with
at least one rubber including at least one diene monomer-containing polymer or copolymer,
5 to 150 phr of at least one reinforcing filler, and
a cure package,
thereby forming a bio-oil-containing rubber composition,
wherein the at least one rubber includes 10 to 90 phr of functionalized polybutadiene having a cis 1,4-bond content of at least 90% and wherein the at least one rubber does not include an oil-extended rubber.

18. The method of claim 17, wherein the recombinant cell comprises an algal cell.

19. The method of claim 17, wherein the functionalized polybutadiene is functionalized with a silicon containing functional group selected from the group consisting of an alkoxysilyl group, an alkylhalosilyl group, a siloxy group, an alkylaminosilyl group, and an alkoxyhalosilyl group.

20. The method of claim 17, wherein the bio-oil has a linoleic acid content of about 45% to about 65% by weight, an oleic acid content of about 20% to about 30% by weight, and a palmitic acid content of about 5% to about 15% by weight.

21. The rubber composition of claim 1, wherein the bio-oil has an oleic acid content of about 55% to about 65% and a linoleic acid content of about 15 to about 20%.

22. The method of claim 10, wherein the bio-oil has an oleic acid content of about 55% to about 65% and a linoleic acid content of about 15 to about 20%.

23. The rubber composition of claim 1, wherein the functionalized polybutadiene is present in an amount of about 50 to about 70 phr.

24. The method of claim 10, wherein the functionalized polybutadiene is present in an amount of about 50 to about 70 phr.

25. The method of claim 17, wherein the functionalized polybutadiene is present in an amount of about 50 to about 70 phr.

* * * * *